US010172592B2

(12) United States Patent
Ward, III et al.

(10) Patent No.: US 10,172,592 B2
(45) Date of Patent: Jan. 8, 2019

(54) ACOUSTIC RESPIRATORY AND NON-RESPIRATORY MOTION DETECTING

(71) Applicant: BioData Innovation Systems, Carlsbad, CA (US)

(72) Inventors: Raymond Joseph Ward, III, Carlsbad, CA (US); Gregory Paul Heldt, Cardiff, CA (US)

(73) Assignee: BIODATA INNOVATION SYSTEMS, Carlsbad, CA (US)

( * ) Notice: Subject to any disclaimer, the term of this patent is extended or adjusted under 35 U.S.C. 154(b) by 623 days.

(21) Appl. No.: 14/730,343

(22) Filed: Jun. 4, 2015

(65) Prior Publication Data

US 2016/0354063 A1 Dec. 8, 2016

(51) Int. Cl.
*A61B 8/08* (2006.01)
*A61B 5/11* (2006.01)
*A61B 5/113* (2006.01)

(52) U.S. Cl.
CPC .......... *A61B 8/5223* (2013.01); *A61B 5/1126* (2013.01); *A61B 5/1135* (2013.01); *A61B 8/08* (2013.01)

(58) Field of Classification Search
CPC ....... A61B 5/1126; A61B 5/1135; A61B 8/08; A61B 8/5223
See application file for complete search history.

(56) References Cited

U.S. PATENT DOCUMENTS

| 4,122,427 A | 10/1978 | Karsh |
| 4,197,856 A | 4/1980 | Northrop |
| 5,220,922 A | 6/1993 | Barany |
| 5,241,515 A | 8/1993 | Harms et al. |
| 5,509,414 A | 4/1996 | Hok |
| 5,638,824 A | 6/1997 | Summers |
| 6,032,769 A | 3/2000 | Daudi |
| 6,062,216 A | 5/2000 | Corn |
| 6,150,941 A | 11/2000 | Geiger et al. |

(Continued)

OTHER PUBLICATIONS

Spriggs, D. R., Sherman, M. L., Michie, H., Arthur, K. A., Imamura, K., Wilmore, D., . . . & Kufe, D. W. (Sep. 7, 1988). Recombinant Human Tumor Necrosis Factor Administered as a 24-Hour Intravenous Infusion. A Phase I and Pharmacologic Study. Journal of the National Cancer Institute, 80(13), 1039-1044.

(Continued)

*Primary Examiner* — Michael T Rozanski
(74) *Attorney, Agent, or Firm* — Hunter Clark PLLC

(57) ABSTRACT

A method of detecting subject respiratory motion and non-respiratory motion includes: transmitting a transmitted signal toward a subject, the transmitted signal being an ultrasound wave, the transmitted signal reflecting off the subject to produce a reflected signal; receiving the reflected signal and converting a form of the reflected signal from ultrasound wave to electrical; comparing the reflected signal to at least a first reference signal to determine at least a first reference phase signal indicative of a first phase difference between the first reference signal and the reflected signal, the at least a first reference signal being associated with the transmitted signal; and analyzing the first reference phase signal for respiratory motion of the subject and non-respiratory motion, the non-respiratory motion including at least one of non-respiratory motion of the subject or motion of an entity other than the subject.

20 Claims, 10 Drawing Sheets

(56) References Cited

U.S. PATENT DOCUMENTS

| | | |
|---|---|---|
| 6,248,068 B1 | 6/2001 | Seabron |
| 7,473,228 B2 | 1/2009 | Griffin et al. |
| 2009/0048500 A1 | 2/2009 | Corn |
| 2011/0121996 A1 | 5/2011 | Griffin et al. |
| 2011/0208060 A1 | 8/2011 | Haase et al. |
| 2013/0060100 A1 | 3/2013 | Wurm et al. |
| 2014/0088373 A1 | 3/2014 | Phillips et al. |

OTHER PUBLICATIONS

Bernstein, G., Cleary, J. P., Heldt, G. P., Rosas, J. F., Schellenberg, L. D., & Mannino, F. L. (Aug. 1993). Response Time and Reliability of Three Neonatal Patient-triggered Ventilators. American Review of Respiratory Disease, 148(2), 358-364. doi:10.1164/ajrccm/148.2.358.

Bernstein, G., Heldt, G. P., & Mannino, F. L. (Nov. 1994). Increased and More Consistent Tidal Volumes during Synchronized Intermittent Mandatory Ventilation in Newborn Infants. American Journal of Respiratory and Critical Care Medicine, 150(5), 1444-1448. doi: 10.1164/ajrccm.150.5.7952573.

Bernstein, G., Knodel, E., & Heldt, G. P. (Oct. 1995). Airway leak size in neonates and autocycling of three flow-triggered ventilators. Critical Care Medicine, 23(10), 1739-1744.

Emeriaud, G., Beck, J., Tucci, M., Lacroix, J., & Sinderby, C. (2006). Diaphragm Electrical Activity During Expiration in Mechanically Ventilated Infants. Pediatric Research, 59(5), 705-710. doi:10.1203/01.pdr.0000214986.82862.57.

Baltag, O., Banarescu, A., & Rau, M. (Jul. 7, 2006). A Comparative Study of Noncontact Sensor for Breathing Monitoring and Sleep Apnea Detection. 5th European Symposium on BioMedical Engineering (ESBME), 4 pp. Retrieved from http://bme.med.upatras.gr/ESBME2006/CD/5th_ESBME_2006_PDFs/Poster_Session/Baltag_Banarescu_full%20paper.pdf.

Beck, J., Reilly, M., Grasselli, G., Qui, H., Slutsky, A. S., Dunn, M. S., & Sinderby, C. A. (Dec. 1, 2011). Characterization of Neural Breathing Pattern in Spontaneously Breathing Preterm Infants. Pediatric Research, 70(6), 607-613. doi:10.1203/PDR.0b013e318232100e.

Mukai, K., Yonezawa, Y., Ogawa, H., Maki, H., & Caldwell, W. M. (Sep. 2009). A remote monitor of bed patient cardiac vibration, respiration and movement. 31st Annual International Conference of the IEEE, Engineering in Medicine and Biology Society (EMBC), 5191-5194. doi:10.1109/IEMBS.2009.5333716.

Heinze, F., Hesels, K., Breitbach-Faller, N., Schmitz-Rode, T., & Disselhorst-Klug, C. (May 6, 2010). Movement analysis by accelerometry of newborns and infants for the early detection of movement disorders due to infantile cerebral palsy. Medical & biological engineering & computing, 48(8), 765-772.

Adde, L., Helbostad, J. L., Jensenius, A. R., Taraldsen, G., Grunewaldt, K. H., & Støen, R. (Aug. 2010). Early prediction of cerebral palsy by computer-based video analysis of general movements: a feasibility study. Developmental Medicine & Child Neurology, 52(8), 773-778. doi:10.1111/j.1469-8749.2010.03629.x.

Yamana, Y., Tsukamoto, S., Mukai, K., Maki, H., Ogawa, H., & Yonezawa, Y. (Aug. 2011). A Sensor for Monitoring Pulse Rate, Respiration Rhythm, and Body Movement in Bed. 33rd Annual International Conference of the IEEE, Engineering in Medicine and Biology Society ( EMBC), 5323-5326. 10.1109/IEMBS.2011.6091317.

Ultrasound BEI. (2012). In ACGIH TLVs and BEls—Threshold Limit Values for Chemical Substances and Physical Agents & Biological Exposure Indices, pp. 126-127. Cincinnati, OH: American Conference of Governmental Industrial Hygienists (ACGIH) Worldwide. Retrieved from http://www.nsc.org/facultyportal/Documents/fih-6e-appendix-b.pdf.

Goldman, L. J. (May 2012). Nasal Airflow and Thoracoabdominal Motion in Children Using Infrared Thermographic Video Processing. Pediatric Pulmonology, 47(5), 476-486. doi:10.1002/ppul.21570.

Terrill, P. I., Wilson, S. J., Suresh, S., Cooper, D. M., & Dakin, C. (Aug. 2012). Application of recurrence quantification analysis to automatically estimate infant sleep states using a single channel of respiratory data. Medical & Biological Engineering & Computing, 50(8), 851-865.

Arlotto, P., Grimaldi, M., Naeck, R., & Ginoux, J. M. (Aug. 20, 2014). An Ultrasonic Contactless Sensor for Breathing Monitoring. Sensors, 14(8), 15371-15386. doi:10.3390/s140815371.

Hu, W., Zhao, Z., Wang, Y., Zhang, H., & Lin, F. (Mar. 2014). Noncontact Accurate Measurement of Cardiopulmonary Activity Using a Compact Quadrature Doppler Radar Sensor. IEEE Transactions on Biomedical Engineering, 61(3), 725-735. doi:10.1109/TBME.2013.2288319.

US 10,172,592 B2

ACOUSTIC RESPIRATORY AND NON-RESPIRATORY MOTION DETECTING

BACKGROUND

Detecting respiration of a patient is desirable, for example to detect abnormal respiration indicating that the patient is in need of attention. There are many existing techniques to detect respiration, such as impedance plethysmography (the standard for hospital monitoring), strain gauges around the patient's chest and/or abdomen, magnetometers, a Respitrace Impedance Plethysmograph (a band around the chest and abdomen), pressure-sensing mattresses, mattresses that sense movement through capacitive sensors, and direct measures of airway flow, either with a mask or through attachment to an artificial airway of a patient. All of these techniques employ physical contact of one or more apparatus with the patient.

Several techniques exist to monitor vital signs of a patient without direct physical contact with the patient. For example, microwave radar may be used with antennas disposed above a prone patient, e.g., attached to a ceiling above a bed on which the patient lies. Other examples include thermal infrared (with the patient's face being uncovered and kept in view of a thermal-sensing camera), and direct video inspection (with the patient being uncovered or covered but with markings placed on the patient). Laser interferometry may also be used to monitor patient respiration if radio interference, interference with materials covering the patient, and laser aiming issues are addressed.

SUMMARY

An example of a method of detecting subject respiratory motion and non-respiratory motion includes: transmitting a transmitted signal toward a subject, the transmitted signal being an ultrasound wave, the transmitted signal reflecting off the subject to produce a reflected signal; receiving the reflected signal and converting a form of the reflected signal from ultrasound wave to electrical; comparing the reflected signal to at least a first reference signal to determine at least a first reference phase signal indicative of a first phase difference between the first reference signal and the reflected signal, the at least a first reference signal being associated with the transmitted signal; and analyzing the first reference phase signal for respiratory motion of the subject and non-respiratory motion, the non-respiratory motion including at least one of non-respiratory motion of the subject or motion of an entity other than the subject.

Implementations of such a method may include one or more of the following features. The analyzing the first reference phase signal for non-respiratory motion comprises: analyzing a combination of a first portion of the first reference phase signal and a second portion of the first reference phase signal for the non-respiratory motion, the first portion of the first reference phase signal being within a first frequency range, the second portion of the first reference phase signal being within a second frequency range, and the second frequency range being separated from the first frequency range. The analyzing the combination comprises determining a dimensionless magnitude associated with the combination. The method further includes: determining that non-respiratory motion of the subject is occurring in response to the dimensionless magnitude being above a first threshold and below a second threshold; and determining that motion of the entity is occurring in response to the dimensionless magnitude being above the second threshold. Determining the dimensionless magnitude comprises dividing a power value of the second portion of the first reference phase signal by a power value of the first portion of the first reference phase signal. The first portion of the first reference phase signal is within a frequency range between 0 Hz and 5 Hz, and the second portion of the first reference phase signal is within a frequency range between 22 Hz and 50 Hz.

Also or alternatively, implementations of the method may include one or more of the following features. The first reference signal and the transmitted signal are both derived from a common electrical drive signal, the comparing comprises comparing the reflected signal to a second reference signal, the second reference signal being a phase-shifted version of the first reference signal, to determine a second reference phase signal indicative of a second phase difference between the second reference signal and the reflected signal, the analyzing the first reference phase signal yields first indicia of respiratory motion of the subject, and the method further includes: analyzing the second reference phase signal for second indicia of respiratory motion of the subject; and forming composite indicia of respiratory motion of the subject comprising the first indicia of respiratory motion of the subject when the first reference phase signal is reliable, and comprising the second indicia of respiratory motion of the subject otherwise. The transmitting comprises transmitting a continuous wave ultrasound signal, having a fixed frequency between 30 KHz and 100 KHz, as the transmitted signal. The analyzing the first reference phase signal for non-respiratory motion comprises comparing a power level in a non-respiratory frequency range portion of the first reference phase signal with a threshold power level.

An example of a motion-detection system includes: a driver configured to produce a drive signal and to produce a transmitter signal from the drive signal and a first reference signal from the drive signal; an ultrasound transmitter communicatively coupled to the driver and configured to transmit a transmitted signal toward a subject in response to the transmitter signal, the transmitted signal being an ultrasound wave; a receiver configured to receive a reflected signal and convert a form of the reflected signal from ultrasound wave to electrical; a phase difference device, communicatively coupled to the driver and the receiver, configured to compare the reflected signal to at least the first reference signal to determine at least a first reference phase signal indicative of a first phase difference between the first reference signal and the reflected signal, the at least a first reference signal being associated with the drive signal; and a signal analyzer communicatively coupled to the phase difference device and configured to analyze the first reference phase signal to determine respiratory motion of the subject and non-respiratory motion, the non-respiratory motion including at least one of non-respiratory motion of the subject or motion of an entity other than the subject.

Implementations of such a system may include one or more of the following features. The signal analyzer comprises non-respiratory motion module configured to analyze a combination of a first frequency portion of the first reference phase signal and a second frequency portion of the first reference phase signal for the non-respiratory motion, the first frequency portion of the first reference phase signal being within a first frequency range, the second frequency portion of the first reference phase signal being within a second frequency range, and the second frequency range being separated from the first frequency range. The non-respiratory motion module is configured to: determine a dimensionless magnitude associated with a combination of the first frequency portion of the first reference signal and the second frequency portion of the first reference phase signal; provide an indication that non-respiratory motion of the subject is occurring if the dimensionless magnitude is above a first threshold and below a second threshold; and provide an indication that motion of the entity is occurring if the dimensionless magnitude is above the second threshold. The non-respiratory motion module is configured to determine the dimensionless magnitude by dividing a power value of the second frequency portion of the first reference phase signal by a power value of the first frequency portion of the first reference phase signal. The first frequency portion of the first reference phase signal is within a frequency range between 0 Hz and 5 Hz, and the second frequency portion of the first reference phase signal is within a frequency range between 22 Hz and 50 Hz.

Also or alternatively, implementations of the system may include one or more of the following features. The the driver is further configured to produce a second reference signal from the drive signal, the second reference signal being a phase-shifted version of the first reference signal, the phase difference device comprises: a first comparator configured to compare the reflected signal to the first reference signal to determine the first reference phase signal and a second comparator configured to compare the reflected signal to the second reference signal to determine a second reference phase signal indicative of a second phase difference between the second reference signal and the reflected signal, and the signal analyzer is configured to form a composite subject respiratory signal by combining a first phase-differential portion of the first reference phase signal with a second phase-differential portion of the second reference phase signal, the first phase-differential portion of the first reference phase signal being within a desirable output range of the first comparator and the second phase-differential portion of the second reference phase signal corresponding to times when the first phase-differential portion of the first reference phase signal is outside the desirable output range of the first comparator. The driver is configured to produce the transmitter signal with a frequency between 35 KHz and 45 KHz. The signal analyzer comprises non-respiratory motion module configured to compare a power level in a non-respiratory frequency range portion of the first reference phase signal with a threshold power level.

Items and/or techniques described herein may provide one or more of the following capabilities, as well as other capabilities not mentioned. Patient respiration, non-respiratory motion of a patient, and motion of an entity other than the patient may be identified and differentiated, and may be done so by a single device in a non-invasive manner. Patient respiration information may be used to implement a synchronizer for mechanical ventilation that may be independent of a mechanical ventilator. Synchronization may be provided between an aerosol generator and a patient's breathing effort, e.g., for more effective delivery of a variety of drugs administered by inhalation including, but not limited to, bronchodilators, antibiotics, chemotherapy agents, and replacement lung surfactants. Pulmonary functions measurements may be aided, e.g., for determination of respiratory system resistance (or conductance), and/or resonant frequency of a respiratory system based on the forced oscillation method. An x-ray machine may be triggered at the end of inspiration. Respiratory rate and/or respiratory effort may be determined. Caretaker movement may be assessed, e.g., for documenting care being given a patient, for charting patient acuity and/or billing, for assessing physiological effects of patient handling, and/or work studies of nursing care and other actioners. Sleep polysomnography may be implemented or aided. Patient overall well-being assessment can be implemented or aided. Patient agitation can be detected and/or assessed. Neurological disorders such as seizures, effects of anti-convulsing therapies, and/or tremulousness can be detected and/or assessed. Drug withdrawal, especially in infants, can be detected and/or assessed. Patient presence, e.g., for elder care, can be detected. Patient comfort and overall well-being can be assessed. Sleep apnea and infant apnea can be detected, and differential diagnosis of obstructive apnea performed. Movement of humans or animals during recovery from anesthesia can be assessed. Movement of animals in laboratory experiments of drugs can be determined. Systemic infections in infants and others may be detected early, e.g., based on decreased movement. Recovery of a respiratory signal after a high-frequency movement is rapid. High resolution, e.g., less than 100 ms, of very short movements typically of non-respiratory movements in infants may be provided. Unambiguous detection of respiratory movement within and across displacements of multiple wavelengths may be provided. Other capabilities may be provided and not every implementation according to the disclosure must provide any, let alone all, of the capabilities discussed. Further, it may be possible for an effect noted above to be achieved by means other than that noted, and a noted item/technique may not necessarily yield the noted effect.

DETAILED DESCRIPTION

Techniques are discussed herein for detecting motion, and in particular detecting respiratory motion of a patient and other motion. For example, in addition to respiratory motion of a patient, non-respiratory motion, including non-respiratory motion of the patient and/or motion of another entity (not the patient), may be detected. The non-respiratory motion may be differentiated and identified. In an example technique to detect motion, a phase difference signal between an ultrasound signal reflected off the patient and a reference signal is determined. Magnitude changes in the phase difference signal are analyzed to determine patient respiratory motion, both the amount of motion and the direction (toward or away from a sensor detecting the reflected signal). Further, a ratio of magnitudes of different frequency portions of the phase difference signal is analyzed to determine the existence of motion other than patient respiratory motion, and to classify any such existing motion. These examples, however, are not exhaustive.

Figure 1:
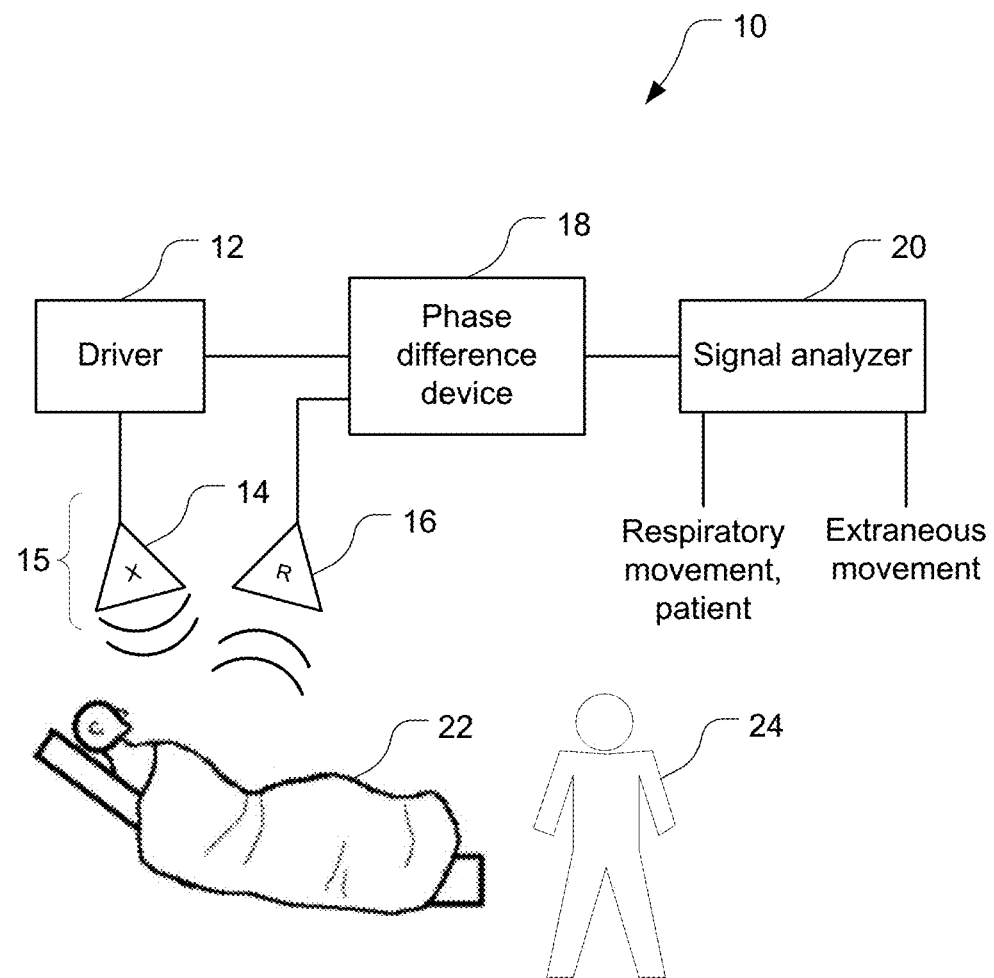
FIG. 1 is a simplified block diagram of a system for determining respiratory motion of a patient, non-respiratory motion of the patient, or motion of another entity.

Referring to FIG. 1, a system 10 includes a driver 12, a transmitter 14, a receiver 16, a phase difference device 18, and a signal analyzer 20. The system 10 is an example of a system configured to detect and identify respiratory motion of a subject or patient 22, non-respiratory motion of the patient 22, and motion of a non-patient entity (e.g., a person 24, a piece of equipment, etc.). The person 24 could be, for example, a caretaker. Although referred to herein throughout as the patient 22, the subject being monitored need not be a patient, and can be a human or an animal. Also, the patient 22, as used herein, includes both the person of the patient 22 and any coverings on the person including clothing (e.g., a hospital Johnny), a bed sheet, a blanket, etc. The system 10 is an ultrasound system configured to determine motion non-invasively. The system 10 is non-invasive in that the patient 22 need not be contacted by any equipment or have any equipment inserted into the patient 22, even though sound waves may penetrate the patient 22. The transmitter 14 preferably makes no physical or electrical contact with the patient 22. The transmitter 14 and the receiver 16 combined may be referred to as a sensor 15. The system 10 is an example of an acoustic respiratory movement sensor (ARMS).

Figure 2:
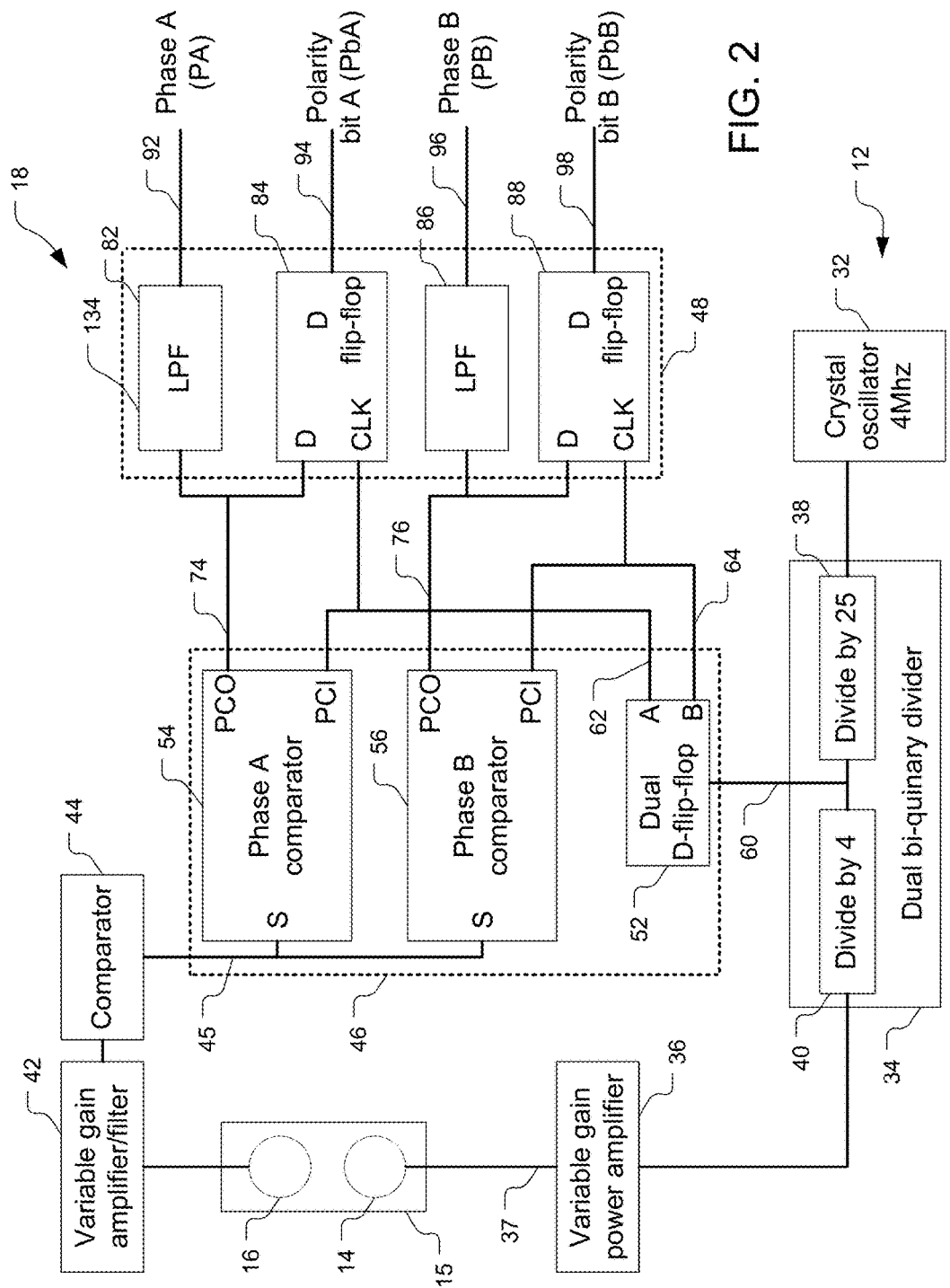
FIG. 2 is a block diagram of an example implementation of the system shown in FIG. 1.

As an example, the system 10 may be used to produce a continuous ultrasound signal and use reflections of the signal from the patient 22 to determine movement of the patient or one or more other entities. For example, the driver 12 may cause the transmitter 14 to produce a continuous ultrasound signal with a frequency between 35 KHz and 45 KHz, preferably about 40 KHz (above the range of human hearing), with the transmitter 14 directed and configured to produce a conical-shaped radiation pattern that covers a torso of the patient 22 in response to a drive signal from the driver 12. The ultrasound signal transmitted by the transmitter 14 will reflect off the patient 22 and the reflected signal may be received by the receiver 16 that is directed and configured to receive ultrasound signals reflected off the patient 22 from the transmitter 14. Movement of the patient 22 will cause the reflected signal to have a slight shift in its phase with respect to the transmitted signal due to the Doppler effect. This phase shift will be detected, and an indication of the phase difference over time provided, by the phase difference device 18. The indication of the phase difference will be processed by the signal analyzer 20 to provide one or more indications of respiratory movement of the patient 22 (corresponding to changes in the phase difference indicated by the phase difference device 18), and/or one or more indications of non-respiratory movement. The non-respiratory movement may include movement of the patient 22 that is not of respiratory origin and/or movement of another entity (i.e., non-patient movement) such as a caretaker of the patient, equipment near the patient 22, etc. An example implementation of the system 10, other than the signal analyzer 20, is shown in FIG. 2, which is discussed in more detail below with respect to the discussion of the components of FIG. 1.

The driver 12 is communicatively coupled to the transmitter 14 and configured to produce an electrical drive signal to induce the transmitter 14 to produce an acoustic ultrasound signal. For example, referring also to FIG. 2, the driver 12 includes a crystal oscillator 32, a drive module 34, and a variable gain power amplifier 36. The oscillator 32 is communicatively coupled to the drive module 34, which is communicatively coupled to the power amplifier 36, which is communicatively coupled to the transmitter 14. The drive module 34 includes, in this example, a dual by-quinary divider that includes a divide-by-25 circuit 38 communicatively coupled to the oscillator 32, and a divide-by-four circuit 40 communicatively coupled to the divide-by-25 circuit 38 and the power amplifier 36. An output of the divide-by-25 circuit 38 is communicatively coupled to the phase difference device 18 that is discussed further below. The oscillator 32 is configured to produce a 4 MHz square wave. The divide-by-25 circuit 38 is configured to divide the signal output by the oscillator 32 by 25 to produce a 160 kHz square wave. The divide-by-four circuit 40 is configured to divide the output signal of the divide-by-25 circuit 38 by four, in this case to produce a 40 kHz square wave that is provided to the variable gain power amplifier 36. The variable gain power amplifier 36 is configured to amplify the signal output by the divide-by-four circuit 40 to produce an amplified signal as a drive output signal 37 of the driver 12.

The drive output signal 37 of the driver 12 is provided to the transmitter 14 by the amplifier 36. The transmitter 14 comprises a transducer configured to convert the electrical signal provided by the power amplifier 36 into an acoustic signal. For example, the transmitter 14 may comprise a piezoelectric transducer. The transmitter 14 is directed toward the patient 22 such that the acoustic signal will be directed to and reflect off of the patient 22.

The receiver 16 comprises a transducer configured to convert the reflected acoustic signal into an electric signal. For example, the receiver 16 may comprise a piezoelectric transducer similar to the transmitter 14. The receiver 16 may comprise more than one transducer, for example, a collection of uncoordinated transducers, an array, such as a phased-array, of transducers, and/or a combination of these, that may provide greater spatial definition of the patient 22 and/or other entity than a single transducer could. The transduced reflected signal is provided as an output of the receiver 16 to the phase difference device 18 as an input.

The phase difference device 18 is configured to determine and provide an indication of a phase difference between a reference signal from the driver 12 and the electrical form of the reflected signal provided by the receiver 16. The reference signal from the driver 12 may be the actual electrical drive output signal 37 provided to the transmitter 14 or another signal related to the drive output signal. For example, in the implementation of the system 10 shown in FIG. 2, the output signal from the divide-by-25 circuit 38 is an intermediate output signal and may be used as a reference signal 60 provided to the phase difference device 18 from the driver 12. The reference signal 60 is likely to be out of phase with the drive reference signal 37, but the phase relationship between the signals 37, 60 will be constant. The phase relationship between the reference signal 60 and the reflected signal will change as the patient 22 moves due to the Doppler effect. This change in the phase relationship may be determined and used by the signal analyzer 20 to determine an indication of respiratory motion of the patient 22. Further, the power in a phase relationship signal, corresponding to the phase relationship between the reference signal 60 and the reflected signal, can be used by the signal analyzer to determine one or more indications of non-respiratory motion either of the patient 22 or another entity.

Further in the example of FIG. 2, the phase difference device 18 includes a variable gain amplifier/filter 42, a comparator 44, a comparison module 46, and a smoothing module 48. The receiver 16 is coupled to the variable gain amplifier/filter 42, which is coupled to the comparator 44, which is coupled to the comparison module 46, which is coupled to the smoothing module 48. The variable gain amplifier/filter 42 is configured to receive the output signal from the receiver 16, that is, the reflected signal in electrical form, to amplify the signal several thousand times, and to filter unwanted signals, e.g., noise produced by other portions of the system 10. The variable gain amplifier/filter 42 is configured to provide the amplified and filtered reflected signal to the comparator 44, which is configured to convert the reflected signal into a reflected signal 45 that is a square wave at logic levels zero and one. The comparator 44 is coupled and configured to provide the reflected signal 45 to the comparison module 46 to determine a phase difference between the reflected signal 45 and the reference signal 60 provided by the driver 12. The reflected signal as used herein includes not only the ultrasound energy reflected off the patient 22, but the various forms of the electrical signal produced in response to the reflected ultrasound, e.g., by the receiver 16, the amplifier/filter 42, and the comparator 44.

In the example implementation of the system 10 shown in FIG. 2, the comparison module 46 includes a dual D-flip-flop 52, a Phase A comparator 54, and a Phase B comparator 56. Other configurations may be used for the comparison module 46, including a single phase comparator being used such as the comparator 54. The flip-flop 52 is coupled to the drive module 34 to receive the reference signal and to convert the reference signal 60 into a Phase A clock signal 62 and a Phase B clock signal 64, each with a frequency of the drive output signal 37, here 40 KHz. The signals 62, 64 are square waves that are out of phase with respect to each other. For example, the signal 62 may be 90° out of phase with the signal 64, with the signal 64 lagging the signal 62, although other phase differences and relationships (leading/lagging) may be used. The example of the signal 62 being 90° out of phase with the signal 64 (i.e., in phase and quadrature phase) is used based upon the particular performance characteristics of the comparators 54, 56. Here, the comparators 54, 56 may be model CD4046 comparators made by Texas Instruments® Incorporated of Dallas, Tex., USA that have substantially linear behavior with respect to phase differences of input signals that produce an output signal between 0.5V and 4.5V. For this example comparator, these output signal voltages correspond to phase differences between about 36 degrees and about 144°, and between about 216° and about 324° (as discussed more fully further below with respect to FIG. 3). Thus, a phase difference of 90° will ensure that a phase difference determined by at least one of the comparators 54, 56 will always be in the linear range of the respective comparator(s) 54, 56. The output signal voltage range of 0.5V to 4.5V is thus a desired operational range of the comparators 54, 56 and may be considered the linear range of the comparators 54, 56. The linear range may be artificially selected with a margin of safety such that the upper and lower thresholds specified for the linear range of the comparators 54, 56 (here, 4.5V and 0.5V of the output signals of the comparators 54, 56) may not be the extremes of the linear capability of the comparators 54, 56, but selected to help reduce noise sensitivity and help ensure or improve accuracy of determined respiratory motion. Thus, even though the comparators 54, 56 may perform linearly for at least some range outside of the designated linear range, the comparators 54, 56 may be considered to be outside their linear ranges if either threshold is exceeded (i.e., the output signal voltage being below the lower threshold or above the upper threshold). Using only outputs of the comparators 54, 56 that are within the linear range helps improve the accuracy of the determined phase relationship between the reflected signal 45 and the reference signal 60 by avoiding high-sensitivity portions of the ranges of the comparators 54, 56 which reduces noise sensitivity of the comparators 54, 56.

The comparators 54, 56 are configured to use the reflected signal 45 provided by the comparator 44 as one input and a respective one of the signals 62, 64 as the other input. Thus, the Phase A comparator 54 uses as inputs the reflected signal 45 (shown as input S) and the Phase A clock signal 62 (shown as a phase comparator input (PCI)), and the Phase B comparator 56 uses as inputs the reflected signal 45 (shown as an input S) from the comparator 44 and the Phase B clock signal 64 (shown as a phase comparator input (PCI)). The Phase A comparator 54 is configured to determine the phase difference between the reflected signal 45 and the Phase A clock signal 62 and the Phase B comparator 56 is configured to determine the phase difference between the reflected signal 45 and the Phase B clock signal 64. The Phase A comparator 54 is configured to provide the phase difference between the reference signal 45 and the Phase A clock signal 62 as an output signal 74 (shown as phase comparator output (PCO)). The Phase B comparator 56 is configured to provide the phase difference between the reference signal 45 and the Phase B clock signal 64 as an output signal 76 (shown as phase comparator output (PCO)). The comparison module 46 is configured and coupled to the smoothing module 48 to provide the output signals 74, 76 to the smoothing module 48.

The smoothing module 48 is configured to provide a smooth signal indicating the phase difference between the reflected signal 45 and the reference signal 60. In the example shown in FIG. 2, the smoothing module 48 is configured to provide smoothed signals that indicate the phase difference between the reflected signal 45 and the Phase A and B signals 92, 96. The smoothing module 48 in this example includes a Phase A low-pass filter (LPF) 82, a Phase A flip-flop 84, a Phase B LPF 86, and a Phase B flip-flop 88. More or fewer filters and flip-flops may be used, for example if only a single comparator is used in the comparison module 46. The Phase A LPF 82 is coupled to the Phase A comparator 54 and configured to smooth, e.g., average, the output signal 74 from the Phase A comparator 54 to produce a Phase A signal 92. The Phase B LPF 86 is coupled to the Phase B comparator 56 and configured to smooth, e.g., average, the output signal 76 from the Phase B comparator 56 to produce a Phase B signal 96. The Phase A LPF 82 and the Phase B LPF 86 are each preferably a resistor-capacitor network with a time constant of 0.1 ms in the example of a 40 kHz drive output signal 37, although other configurations with other time constants, including longer or shorter time constants, may be used. The flip-flops 84, 88 are D flip-flops that are coupled to receive the Phase A output signal 74 and the Phase B comparator output signal 76, respectively, at respective data inputs and to receive the Phase A clock signal 62 and the Phase B clock signal 64, respectively, at respective clock signal inputs. The flip-flops 84, 88 will thus produce, respectively, a polarity bit A signal 94 and a polarity bit B signal 98 indicative of a phase quadrant in which the respective phase signal is, and that can be used to ensure the correct polarity of a respiratory movement signal as discussed further below.

As discussed above, the Phase A clock signal 62 and the Phase B clock signal 64 are out of phase with respect to each other. Because the Phase A comparator 54 and the Phase B comparator 56 both compare these signals respectively to the same signal, i.e., the reflected signal 45, the Phase A signal 92 and the Phase B signal 96 will be out of phase with respect to each other by the same amount as the clock signals 62, 64.

Figure 3:
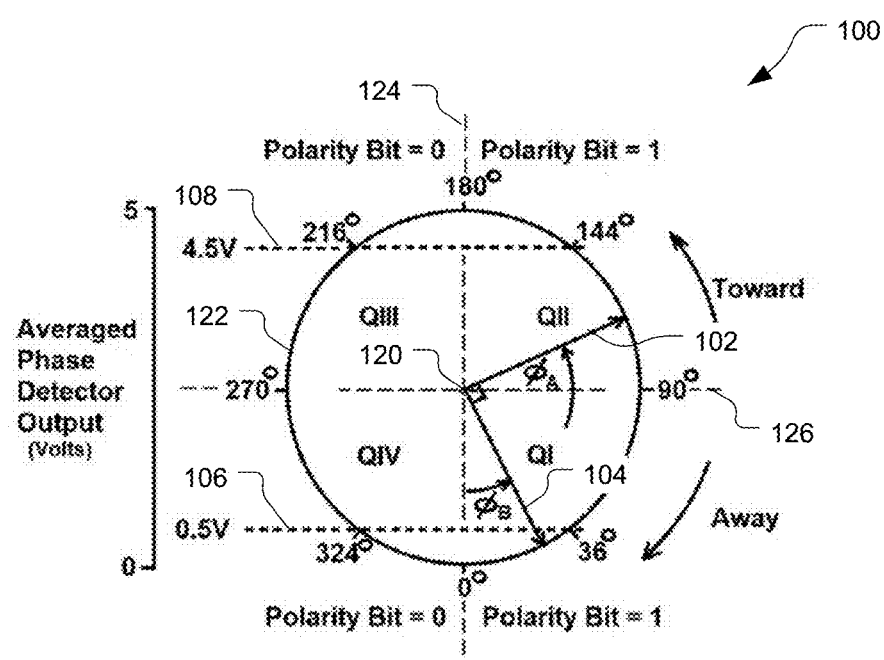
FIG. 3 is a phase versus voltage characteristic of examples of averaged phase signals produced by comparators shown in FIG. 2.

Referring also to FIG. 3, in a phase space 100 the Phase A signal 92 (shown as $\phi_A$) is 90° out of phase with the Phase B signal 96 (shown as $\phi_B$), with the signal 96 ($\phi_B$) lagging or leading the signal 92 ($\phi_A$) depending upon whether motion of the patient 22 is toward or away from the receiver 16. FIG. 3 is a phase-space diagram of phase difference with respect to the reflected signal 45, with phases being an angle about a center point 120, and a vertical position on a phase circle 122 corresponding to a voltage value of a corresponding phase signal, here the Phase A signal 92 or the Phase B signal 96. The bottom of a vertical axis has been chosen to be 0°, or no relative phase difference between the transmitted and received signals, with a top of the vertical axis 124 therefore being 180° of phase difference. Consequently, a right-hand side of a horizontal axis 126 corresponds to 90° of phase difference and a left-hand side of the horizontal axis 126 corresponds to 270° of phase difference. The Phase A signal 92 is shown as a Phase A vector 102 and the Phase B signal 96 is shown as a Phase B vector 104.

As the patient 22 moves toward the sensor 15, the phase of the reflected signal leads that of the transmitted signal, since the time to return is decreased. As the patient 22 moves away from the sensor 15, the phase of the reflected signal lags that of the transmitted signal, since the time to return is increased. As the patient 22 moves toward the sensor 55, the vectors 102, 104 are both moving counter-clockwise in the phase space. Both the Phase A and Phase B signals 92, 96 are increasing when both vectors 102, 104 are in quadrant 1 (QI) and quadrant 2 (QII) of the phase space 100, and are decreasing when both the vectors 102, 104 are in quadrant 3 (QIII) and quadrant 4 (QIV) with continued counter-clockwise rotation. The polarity bit A and B signals 94, 98 are set by the flip-flops 84, 88 that detect whether the trailing edge of the reflected signal leads the trailing edge of the transmitted signal, as in QI and QII, or lags the trailing edge of the transmitted signal, as in QIII and QIV, being set to 1 in QI and QII, and 0 in QIII and QIV. In this way, the position of the two vectors 102, 104 can be unambiguously determined from the polarity bit A and B signals 94, 98 so as determine the direction of changes in the Phase A signal 92 and the Phase B signal 96.

From FIG. 3, the behavior of the signals 92, 96 can be seen with reference to the vectors 102, 104. If the Phase A vector 102 is in QIII, then the Phase B vector 104 will be in QII. During movement of the Phase A vector 102 counter-clockwise through QIII (the patient 22 moving toward the sensor 15), the Phase A signal 92 is decreasing, and the Phase B signal 96 is increasing. When the Phase A vector 102 enters QIV, the Phase B vector 104 enters QIII. With further movement of the patient 22 toward the sensor 15 with the Phase A vector entering QI, the Phase A signal 92 will increase and the Phase B signal 96 will decrease. When the Phase A vector 102 is in QI or QII, when the flip-flop 84 is clocked, the Phase A output signal 74 will be a logical 1 and thus the polarity bit A signal 94 will be set to a logical 1. The same applies for the Phase B polarity bit signal 98. When the Phase A vector 102 is in QIII or QIV, when the flip-flop 84 is clocked, the Phase A output signal 74 will be a logical 0 and thus the polarity bit A signal 94 will be set to a logical 0. The same applies for the Phase B polarity bit signal 98.

Lines 106, 108 indicate threshold levels, here 0.5V and 4.5V, of averaged phase signal levels corresponding to the linear range limits of the comparators 54, 56 in the example of the comparators 54, 56 being model CD4046 comparators made by Fairchild Semiconductor Corporation. Below the line 106 or above the line 108, a large phase angle change results in a small voltage change, and thus these phase angle ranges are preferably avoided so that the outputs of the comparators 54, 56 are only used when the comparators 54, 56 are in their linear ranges to reduce noise. The phase angles at 0.5V corresponding to the line 106 are 36° and 324° in QI and QIV, and the phase angles at 4.5V corresponding to the line 108 are 144° and 216° in QII and QIII, respectively. Since the Phase A vector 102 and the Phase B vector 104 are fixed at 90° from each other, when the Phase A vector 102 (corresponding to the Phase A signal 92) enters a bottom or top out-of-specification zone, i.e., below the line 106 or above the line 108 (with the Phase A signal 92 below 0.5V or above 4.5V), the Phase B vector 104 is within an allowed zone between the lines 106, 108. The signal analyzer 20, as discussed more fully below, is configured to detect whether the Phase A vector 102 (the Phase A signal 92) is in the allowed zone, and if not, to select the Phase B signal 96 for computations of respiratory motion. The range of 0.5V to 4.5V is an example only and other ranges may be used, either for the example comparators 54, 56 and/or other comparators. With the range of 0.5V to 4.5V chosen, and with the Phase A signal 92 used as the default signal, the Phase A signal 92 will be predominantly used for computations for respiratory motion.

Figure 4:
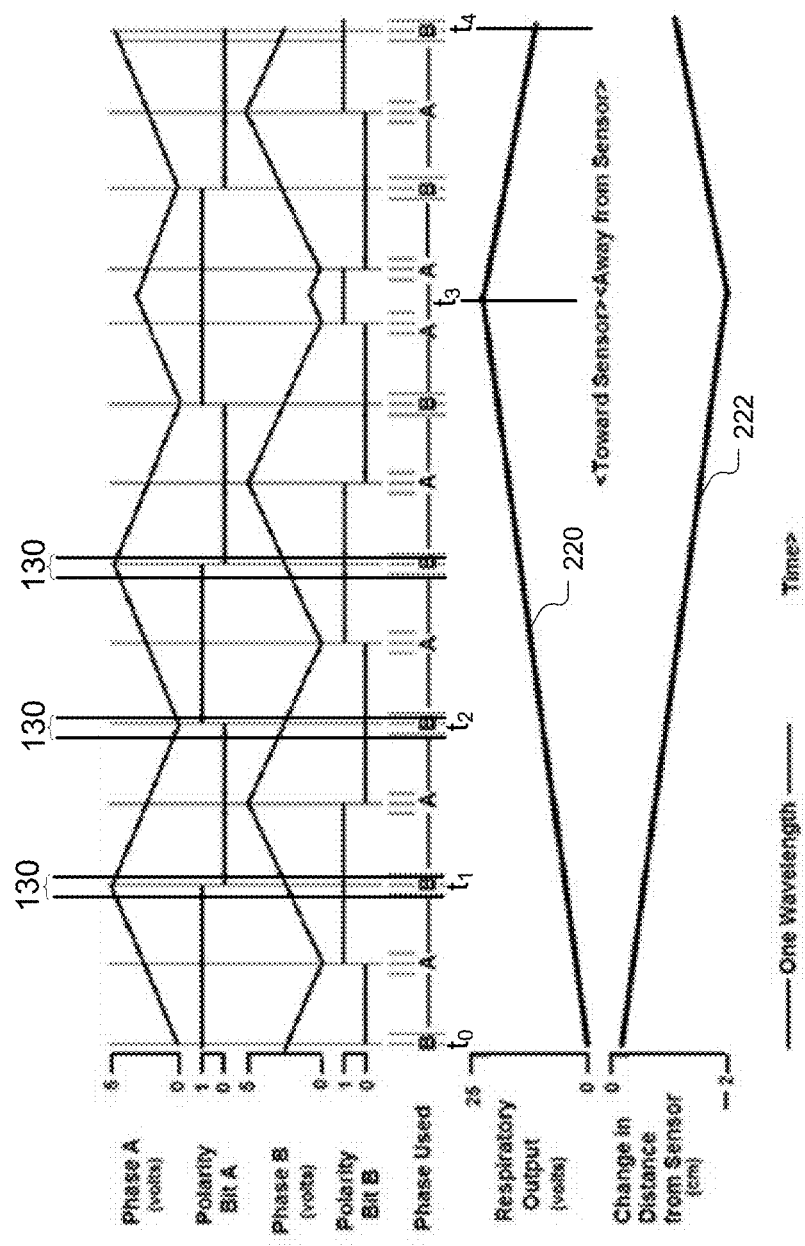
FIG. 4 is a timing diagram of output signals of a phase difference device shown in FIG. 1 corresponding to motion of the patient shown in FIG. 1.

Referring also to FIG. 4, a timing diagram 200 shows relative timing of the Phase A signal 92, the polarity bit A signal 94, the Phase B signal 96, the polarity bit B signal 98 corresponding to motion of the patient 22 relative to the sensor 15, and an indication of which of the phase signals 92, 96 is used at any given time. In FIG. 4, the patient 22 moves toward the sensor 15 for about 2.5 wavelengths, then reverses and moves away from the sensor 15 for just under one wavelength. This is the equivalent of counter-clockwise movement of the phase vector approximately 900 degrees, and then clockwise movement of approximately 300 degrees. At a time $t_0$, the Phase A signal 92 increases from 0V toward 5V as the patient 22 moves toward the sensor 15. At a time $t_1$, the Phase A signal 92 reaches 5 V, and reverses direction, returning from 5V at the time $t_1$ to 0V at a time $t_2$. This pattern continues until that time $t_3$ when the patient 22 stops moving toward the center 15 and reverses direction, moving away from the sensor 15 from the time $t_3$ until a time $t_4$. From the time $t_0$ until the time $t_3$, with the patient 22 moving toward the sensor 15, the Phase B signal 96 lags the Phase A signal 92 (i.e., the Phase A signal 92 leads the Phase B signal 96) by 90°. From the time $t_3$ until the end of the record, with the patient 22 moving away from the sensor 15, the Phase B signal 96 leads the Phase A signal 92 (i.e., the Phase A signal 92 lags the Phase B signal 96) by 90°. While the patient 22 is moving toward the sensor 15, the polarity bit A signal 94 is a logical 1 during time intervals when voltage of the Phase A signal 92 is increasing and a logical 0 during time intervals when the voltage of the Phase A signal 92 is decreasing. The same applies for the polarity bit B signal 98 with respect to the Phase B signal 96. Conversely, while the patient 22 is moving away from the sensor 15, the polarity bit A signal 94 is a logical 1 during time intervals when the voltage of the Phase A signal 92 is decreasing and a logical 0 during time intervals when the voltage of the Phase A signal 92 is increasing. The phase diagram in FIG. 3 shows the correspondence between the polarity bit and the quadrant of the phase vector. The same applies for the polarity bit B signal 98 with respect to the Phase B signal 96. Out-of-specification conditions are indicated by intervals 130 during which the Phase B signal 96 will be used, while during all other times, the Phase A signal 92 will be used for the example implementation being discussed herein.

The phase relationship between the reference signal 60 and the reflected signal provided by the phase difference device 18, and in particular the comparison module 46 and the smoothing module 48, may be used by the signal analyzer 20 to determine respiratory motion of the patient 22 and non-respiratory motion either of the patient 22 or another entity. For example, the change in the phase relationship can be determined, e.g., as discussed further below by differentiating one or more phase relationship signals provided by the phase difference device 18, as an indication of the motion of the patient 22.

Figure 5:
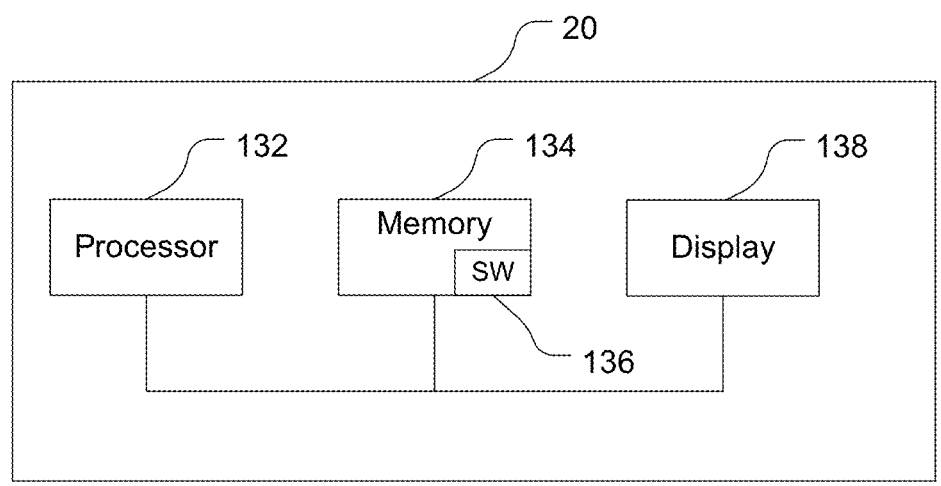
FIG. 5 is a block diagram of components of a signal analyzer shown in FIG. 1.

Referring to FIG. 5, an example of the signal analyzer 20 comprises a computer system including a processor 132, a non-transitory memory 134 including (optionally) software 136, and a display 138. The processor 132 is preferably an intelligent device, e.g., a personal computer central processing unit (CPU) such as those made or designed by QUALCOMM®, Intel® Corporation, ARM®, or AMD®, a microcontroller, an application specific integrated circuit (ASIC), etc. The processor 132 could comprise multiple separate physical entities that can be distributed in the signal analyzer 20. The memory 134 may include random access memory (RAM) and read-only memory (ROM). The memory 134 is a processor-readable storage medium that may store the software 136 which is processor-readable, processor-executable software code containing instructions that are configured to, when executed, cause the processor 132 to perform various functions described herein (although the description may refer only to the processor 132 performing the functions). Alternatively, the software 126 may not be directly executable by the processor 132 and instead may be configured to cause the processor 132, e.g., when compiled and executed, to perform the functions. The software 136 can be loaded onto the memory 134 by being downloaded via a network connection, uploaded from a disk, etc. The display 138 is a liquid-crystal display (LCD) (e.g., a thin-film transistor (TFT) display), although other forms of displays are acceptable, e.g., a cathode-ray tube (CRT). The processor 132, the memory 134, and the display are communicatively coupled to each other.

Figure 6:
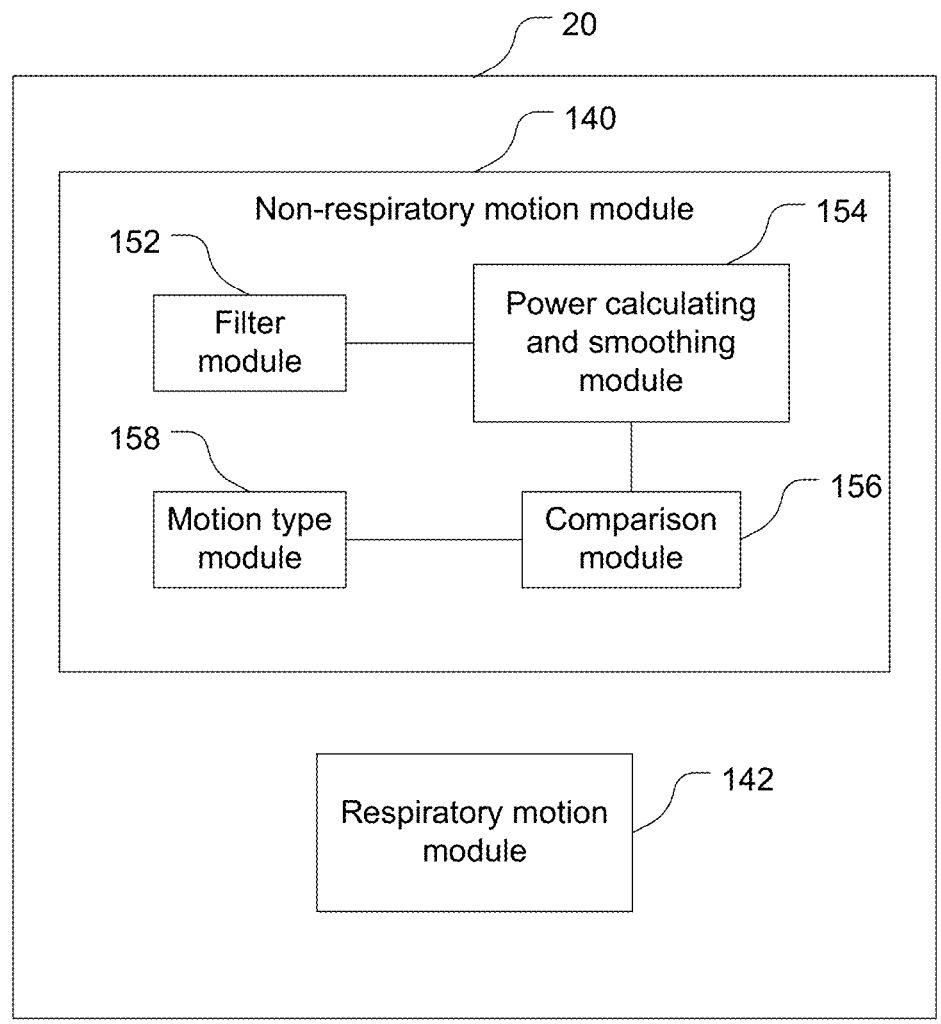
FIG. 6 is a functional block diagram of the signal analyzer shown in FIG. 5.

Referring to FIG. 6, with further reference to FIGS. 1 and 5, the signal analyzer 20 includes a non-respiratory motion module (means for determining non-respiratory motion) 140 and a respiratory motion module (means for determining respiratory motion) 142. The non-respiratory motion module 140 includes a filter module (means for filtering) 152, a power calculating and smoothing module (means for calculating power and smoothing) 154, a comparison module (means for determining a comparison) 156, and a motion type module (means for determining a motion type) 158. The modules 140 (including the modules 152, 154, 156, 158), 142 are functional modules implemented by the processor 132 and the software 136 stored in the memory 134. Thus, reference to any of the modules 140, 142, 152, 154, 156, 158 performing or being configured to perform a function is shorthand for the processor 132 performing or being configured to perform the function in accordance with the software 136 (and/or firmware, and/or hardware of the processor 132). Alternatively, one or more of the modules 142, 152, 154, 156 and 158 could be implemented using analog circuitry without microprocessor support, or using a combination of analog circuitry and processor support. Similarly, reference to the processor 132 performing a function discussed with respect to the signal analyzer 20, is equivalent to the respective module(s) 140, 142, 152, 154, 156, 158 performing the function.

The non-respiratory motion module 140 is configured to determine if the patient 22 is moving aside from breathing, i.e., if non-respiratory motion of the patient 22 is present, and if there is motion present of an entity other than the patient 22. The module 140 is configured to determine if either of these types of motion is present, and to distinguish between and provide indications of these types of motion by determining and analyzing a normalized magnitude of a frequency range of the phase relationship between the reference signal and the reflected signal. The phase relationship between the reference signal and the reflected signal is normalized to a frequency range associated with respiration of the patient 22.

Figure 7:
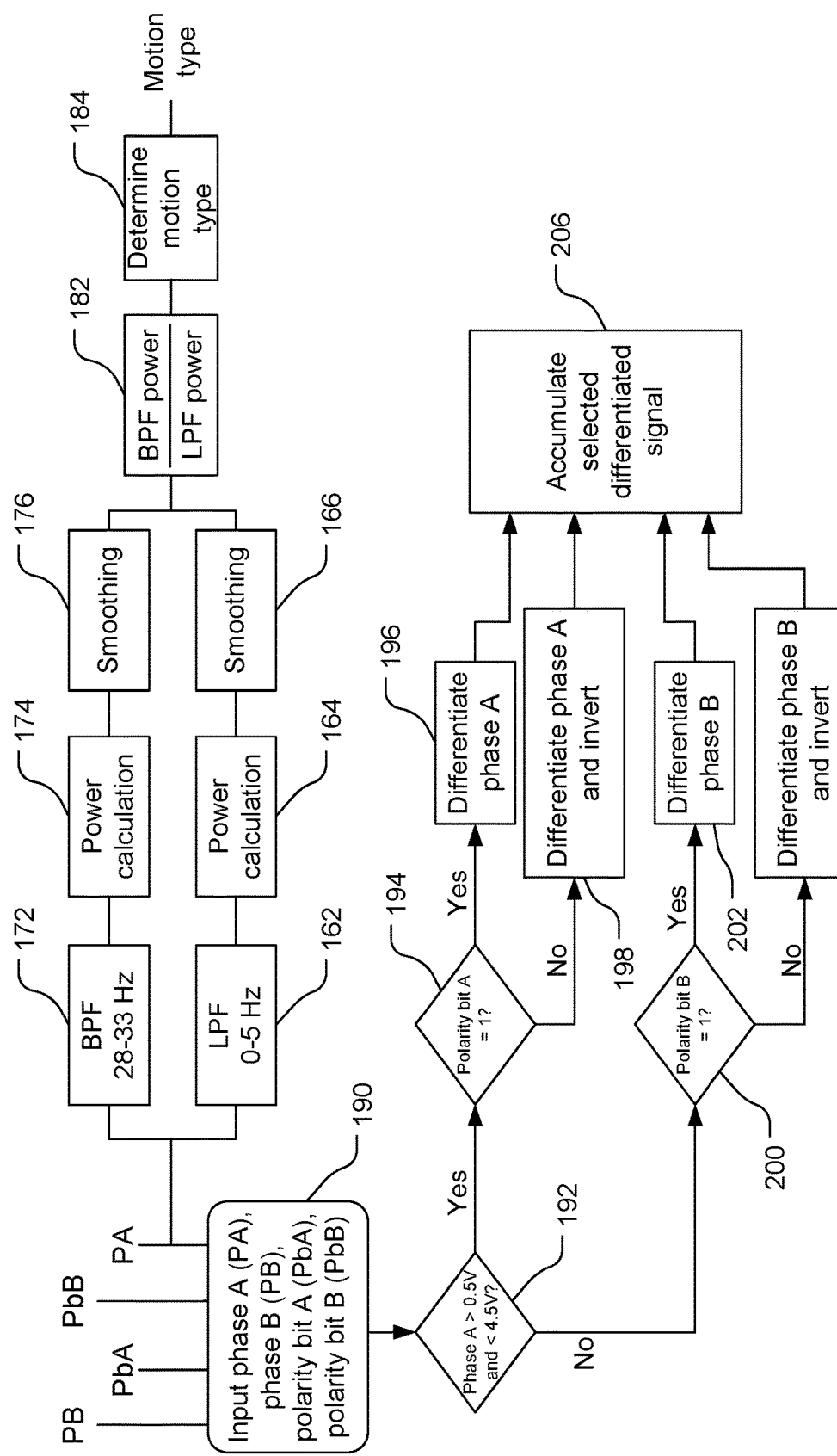
FIG. 7 is a block flow diagram of an example algorithm implemented by the signal analyzer shown in FIG. 6.

The filter module 152 is configured to separate different frequency ranges of the phase relationship between the reference signal and the reflected signal as indicated by the phase difference device 18. Referring also to, and in an example implementation of an algorithm implemented by the signal analyzer 20 shown in, FIG. 7, the filter module 152 is configured to filter the Phase A signal 92 from the phase difference device 18 into two frequency bands. In the example shown in FIG. 7, at stages 162, 172 the filter module 152 is configured to low-pass filter the Phase A signal 92 into a respiration frequency band and to band-pass filter the Phase A signal 92 into a non-respiration frequency band. The respiration frequency band is a range of frequencies that are likely to include frequencies of respiration of the patient 22. For example, as shown in FIG. 7 at a stage 162, the respiration frequency band may be from 0 Hz to 5 Hz, which is a band associated with respiration of an infant. The non-respiration frequency band is a range of frequencies that are likely to include frequencies of non-respiratory motion of entities other than the patient 22. For example, as shown in FIG. 7 at a stage 172, the non-respiration frequency band may be between 22 Hz and 50 Hz, and preferably from 28 Hz to 33 Hz as shown. The respiration frequency band is different from, and preferably separated from the non-respiration frequency band. Preferably, the LPF 162 suppresses signals in the non-respiration frequency band by at least 10 dB. Also preferably, the BPF 172 suppresses signals in the respiration frequency band by at least 10 dB.

The power calculating and smoothing module 154 is configured to determine power contained in the filtered signal portions from the filter module 152 and smooth the determined values for use in a comparison of the two powers. As shown in stages 164 and 166, the module 154 is configured to calculate a power in the respiration-band filtered signal determined at stage 162, and to smooth (e.g., average) the calculated power over time to determine a respiration power value. Similarly, as shown in stages 174 and 176, the module 154 is configured to calculate a power in the non-respiration-filtered signal determined at stage 172, and to smooth (e.g., average) the calculated power over time to produce a non-respiration power value.

The comparison module 156 is configured to compare the non-respiration power value to the respiration power value from the power calculating and smoothing module 154 to determine motion parameter value. As shown at stage 182 of FIG. 7, the module 156 is configured to calculate a comparison of signal power in the non-respiration frequency band and signal power in the respiration frequency band, here calculate a ratio, of the non-respiration power value to the respiration power value to determine the motion parameter value, which is a dimensionless number, a dimensionless magnitude of the power ratio.

The motion type module 158 is configured analyze the motion parameter value from the ratio module 156 to determine which type of non-respiratory motion, if any, is present in a region detectable by the sensor 15 (i.e., a field of "view" of the sensor 15). The module 158 can classify non-respiratory motion into non-respiratory patient motion, or motion of an entity other than the patient 22 (a non-patient entity, i.e., a non-subject entity). For example, the motion type module 158 can classify different motions based upon threshold values for the motion parameter value. For example, the module 158 may determine that no non-respiratory motion is present if the motion parameter value is below 0.004, that there is non-respiratory motion of the patient 22 if the motion parameter value is in a range from 0.004 to 0.02, or that there is non-respiratory motion of an entity other than the patient 22 if the motion parameter value is above 0.02. As shown at stage 184, the module 156 is configured to provide an output that indicates the type(s) of motion present or the lack of non-respiratory motion being present. Alternatively, the module 156 may be configured to indicate that non-respiratory motion is present without indicating which type of non-respiratory motion is present.

The respiratory motion module 142 is configured to process the indication, provided by the phase difference device 18, of the phase relationship between the reflected signal and the reference signal to determine and provide an indication of respiratory motion of the patient 22. In particular, the respiratory motion module 142 is configured to determine a change in the phase relationship between the reflected signal and the reference signal to produce time-varying information indicative of the patient's respiratory motion. This time-varying information may be in the form of a time-varying voltage that may be plotted to show the patient's respiratory motion. For example, a trace 220 shows the time-varying voltage corresponding to an example where the patient 22 has constant-speed respiratory motion, and a trace 222 shows the motion in distance as a function of time, here the motion being 2 cm moving toward the sensor 15 and then about 1 cm moving away from the sensor 15.

FIG. 7 shows stages of an example algorithm of the respiratory motion module 142 for the example implementation of the driver 12, the transmitter 14, the receiver 16, and the phase difference device 18 shown in FIG. 2. The respiratory motion module 142 is configured to receive as inputs, at a stage 190, the Phase A signal 92, the polarity bit A signal 94, the Phase B signal 96, and the polarity bit B signal 98 to determine the respiratory motion of the patient 22. In this example, the module 142 is configured to use the Phase A signal 92 while the Phase A comparator 54 is in a linear operation range, here while the Phase A signal 92 is between 0.5V and 4.5V. That is, the module 142 is configured to use the Phase A signal 92 unless the Phase A signal 92 is below 0.5V or above 4.5V, i.e., unless the Phase A comparator 54 is outside a linear operation range. Thus, as shown by a stage 192, the module 142 is configured to determine whether the Phase A signal 92 is within a range from 0.5V to 4.5V.

The respiratory motion module 142 is configured to respond to the Phase A signal 92 being between 0.5V and 4.5V by processing the Phase A signal 92 to determine respiratory motion of the patient 22, and being below 0.5V or above 4.5V by processing the Phase B signal 94 to determine respiratory motion of the patient 22. The module 142 is configured to respond to the Phase A signal 92 being between 0.5V and 4.5V by determining, at stage 194, whether the polarity bit A signal 94 is a logical 1 or a logical 0. The module 142 is configured to respond to the polarity bit A signal 94 being a logical 1 by differentiating, at stage 196, the Phase A signal 92 to determine the change in the Phase A signal 92 which is an indication of the patient's respiratory motion with the polarity bit A signal 94 being a logical 1. The module 142 is configured to respond to the polarity bit A signal 94 being a logical 0 by differentiating and then inverting, at stage 198, the Phase A signal 92 to determine the inverse of the change in the Phase A signal 92 which is an indication of the patient's respiratory motion with the polarity bit A signal 94 being a logical 0. The module 142 is configured to respond to the Phase A signal 92 being below 0.5V or above 4.5V by determining, at stage 200, whether the polarity bit B signal 98 is a logical 1 or a logical 0. The module 142 is configured to respond to the polarity bit B signal 98 being a logical 1 by differentiating, at stage 202, the Phase B signal 96 to determine the change in the Phase B signal 96 which is an indication of the patient's respiratory motion with the polarity bit B signal 98 being a logical 1. The module 142 is configured to respond to the polarity bit B signal 98 being a logical 0 by differentiating and then inverting, at stage 204, the Phase B signal 96 to determine the inverse of the change in the Phase B signal 96 which is an indication of the patient's respiratory motion with the polarity bit B signal 98 being a logical 0.

The respiratory motion module 142 is configured to aggregate the determined indications of the patient's respiratory motion to provide a composite signal indicative of the respiratory motion of the patient 22. The module 142 is configured to accumulate, at stage 206, the differentiated, or inverted and differentiated signals to form a composite signal that will indicate the patient's respiratory motion as a function of time. This signal can be plotted to provide a visual indication of the respiration, for example as shown by the trace 220 in FIG. 4.

Figure 8:
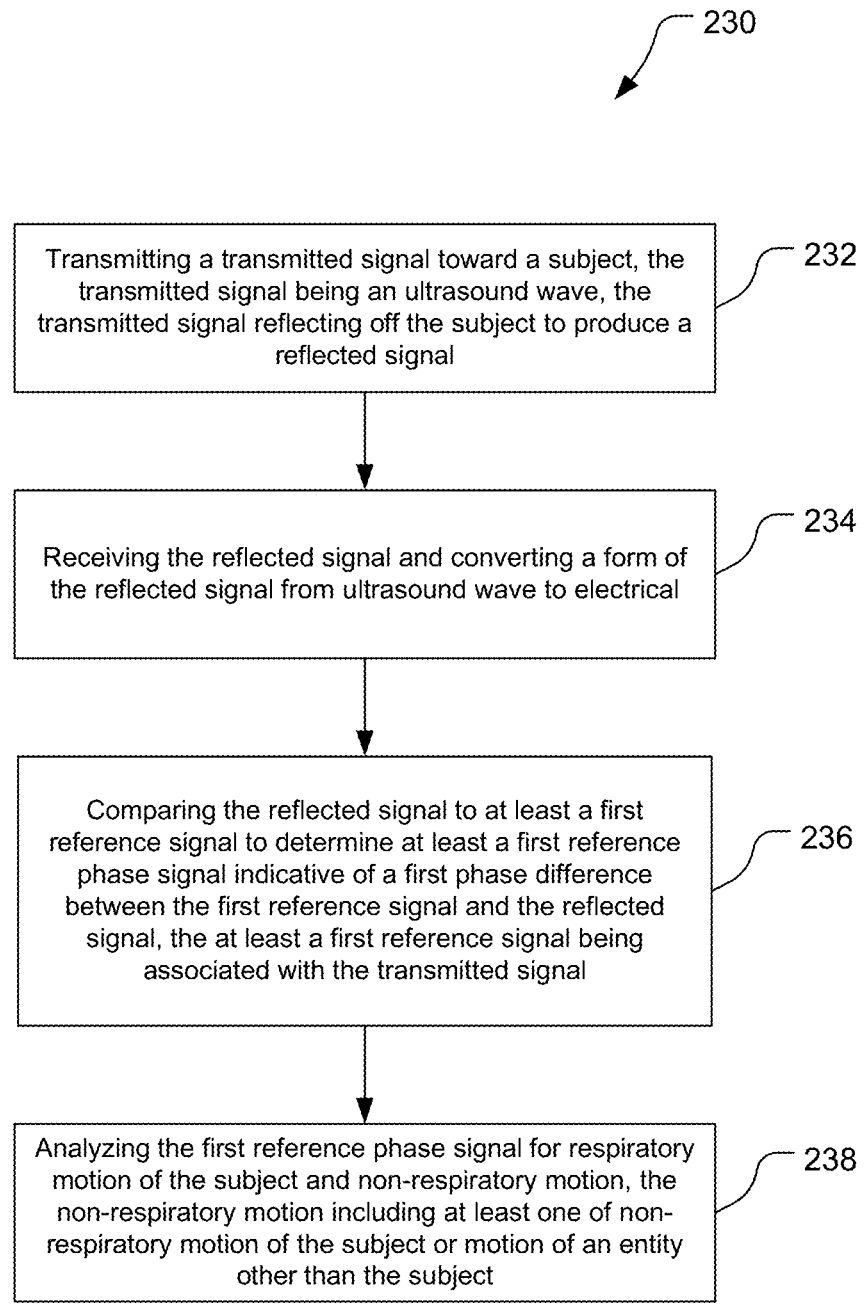
FIG. 8 is a block flow diagram of a process of detecting respiratory and non-respiratory motion.

Referring to FIG. 8, with further reference to FIGS. 1-7, a process 230 of detecting respiratory and non-respiratory motion includes the stages shown. The process 230 is, however, an example only and not limiting. The process 230 can be altered, e.g., by having stages added, removed, rearranged, combined, performed concurrently, and/or having single stages split into multiple stages.

At stage 232, the process 230 includes transmitting a transmitted signal toward a subject, the transmitted signal being an ultrasound wave, the transmitted signal reflecting off the subject to produce a reflected signal. The driver 12 produces and provides the drive signal 37 to the transmitter 14 of the sensor 15. The transmitter 14 transduces the drive signal 37 into an acoustic ultrasound wave that is transmitted toward the patient 22 as a transmitted signal. The transmitted signal is preferably a continuous wave, e.g., with energy being transmitted by the transmitter 14 nearly uninterrupted (e.g., more than 95% as a function of time). Further, the transmitted signal preferably has a frequency between 30 KHz and 100 KHz, and more preferably between 35 KHz and 45 KHz, and more preferably about 40 KHz. A portion of the acoustic ultrasound signals reflect off the patient 22 as a reflected signal.

At stage 234, the process 230 includes receiving the reflected signal and converting a form of the reflected signal from ultrasound wave to electrical. The receiver 16 receives the reflected signal and transduces the reflected signal from an acoustic ultrasound wave to an electrical signal.

At stage 236, the process 230 includes comparing the reflected signal to at least a first reference signal to determine at least a first reference phase signal indicative of a first phase difference between the first reference signal and the reflected signal, the at least a first reference signal being associated with the transmitted signal. For example, the comparison module 46 compares the reflected signal 45 with the reference signal 60 provided by the driver 12, with the reflected signal 45 and the reference signal 60 having the same, or nearly the same, frequency except for, e.g., changes due to the Doppler effect and variations within the tolerance of the crystal oscillator 32. The comparison module 46 produces a signal indicative of the phase relationship between the reflected signal 45 and the reference signal 60. In the example of FIG. 2, the comparison module 46 produces the Phase A signal 92, the polarity bit A signal 94, the Phase B signal 96, and the polarity bit B signal 98 that can be combined to form a signal that is reliably indicative of the phase relationship of the reflected signal 45 to the reference signal 60 over an entire range of phase differences. This signal may be unambiguously indicative of this phase relationship over multiple wavelengths of motion.

At stage 238, the process 230 includes analyzing the first reference phase signal for indicia of respiratory motion of the subject and at least one of indicia of non-respiratory motion of the subject or indicia of motion of an entity other than the subject. For example, the respiratory motion module 142 of the signal analyzer 20 analyzes the Phase A signal 92 to determine an indication of respiratory motion of the patient 22. The module 142 determines changes in the Phase A signal 92 over time to form a signal that represents the respiratory motion of the patient 22. For the example implementation of the driver 12 and the phase difference device 18 shown in FIG. 2, the respiratory motion module 142 analyzes and combines the Phase A signal 92 over a linear operation range of the Phase A comparator 54 with the Phase B signal 96 during times when the Phase A comparator is outside the desired operational range to determine the signal that represents the respiratory motion of the patient 22. Further, the non-respiratory motion module 140 of the signal analyzer 20 determines the magnitude of power in the Phase A signal 92 for different frequency ranges (e.g., 22-50 Hz (and preferably 28-33 Hz) and 0-5 Hz), compares these power magnitudes, and determines the presence and type of non-respiratory motion, e.g., by comparing a ratio of the power magnitudes to thresholds for different types of non-respiratory motion (motion by the patient 22 that is not respiration or non-patient motion).

Figure 9:
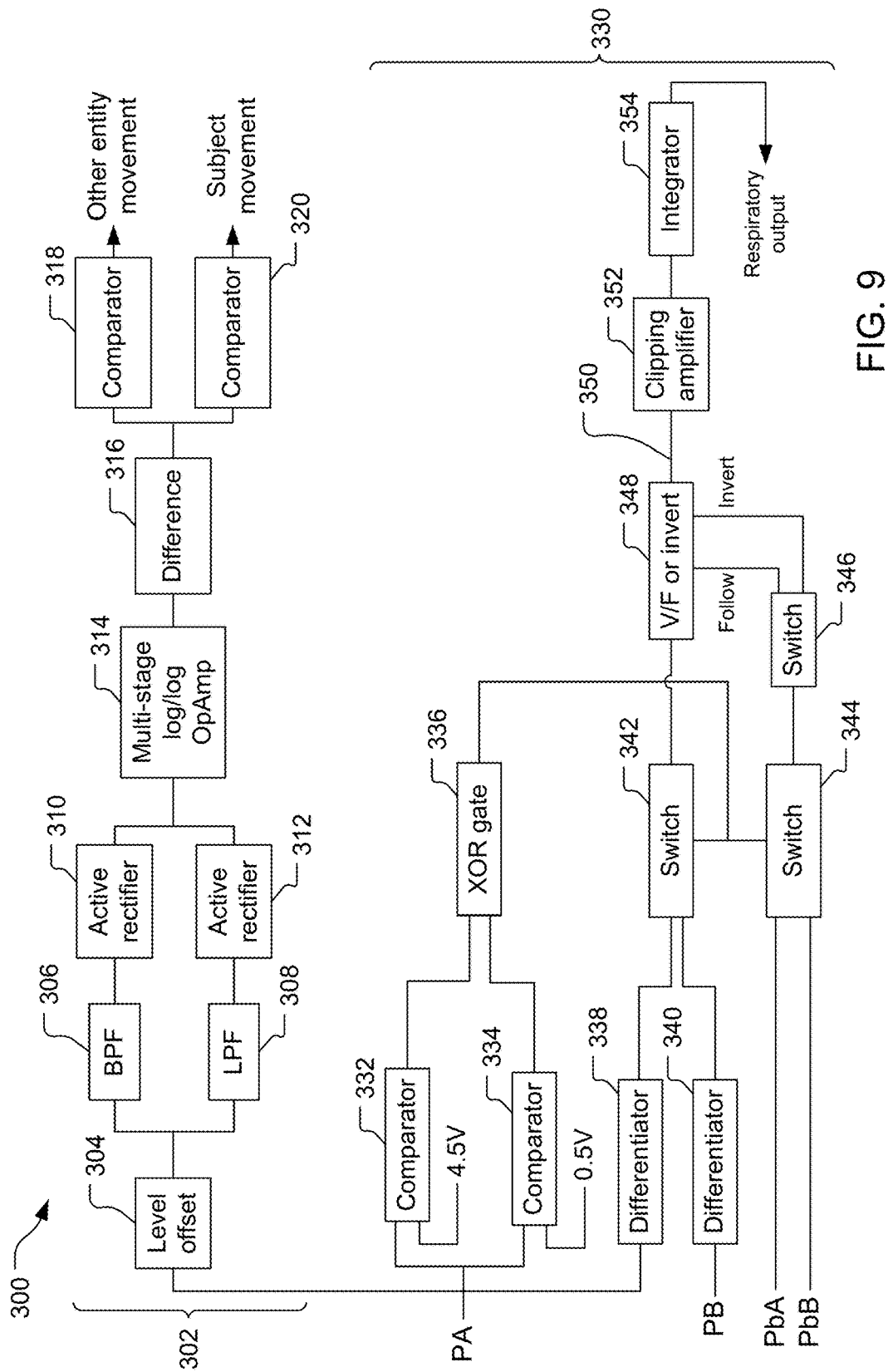
FIG. 9 is a block diagram of an analog implementation of the signal analyzer shown in FIG. 6.

Referring to FIG. 9, with further reference to FIGS. 1, 2, 6, and 7, a mixed analog-and-digital circuit 300 implementation of the non-respiratory motion module 140 and the respiratory motion module 142 shown in FIG. 6 includes the components shown. A section 302 implements the non-respiratory motion module 140 and a section 330 implements the respiratory motion module 142. The circuit 300 is configured to perform the example algorithm discussed above with respect to FIG. 7 without use of a computer or microprocessor. The circuit 300 can be realized with standard high-grade operational amplifiers that are commercially available, such as the TLE 2081, TLE 2082, or TLE 2084 integrated circuits made by Texas Instruments Incorporated of Dallas, Tex., USA. These example circuits have very low noise, input offset null, a high slew rate, and more than sufficient output voltage ranges. For some of the components, a general purpose operational amplifier is used, such as model MC3403 made by Texas Instruments. The components are preferably operated with a linear, stabilized +/−9-18 VDC power supply (not shown) and a 5 VDC power supply for the digital circuitry.

In this example, the filter module 152 of the non-respiratory module 140 includes a level offset amplifier 304, a band-pass filter (BPF) 306, and a low-pass filter (LPF) 308. The Phase A signal (PA) from the phase difference device 18 is connected to the level offset amplifier 304 that offsets the PA signal, with a range of 0-5V, to +/−2.5V. The level offset amplifier 304 may be implemented by a model MC3403 or TLE 208X series operational amplifier made by Texas Instruments. The offset signal is passed to the BPF 306 and the LPF 308. The BPF 306 is preferably an 8-pole filter with a center frequency of 30.4 Hz. The LPF 308 is preferably an 8-pole filter with a corner frequency of 5 Hz. Examples of the filters 306, 308 can be obtained from Frequency Development, Inc., Ottawa, Ill., USA, in a variety of implementations with appropriate transfer characteristics, such as the DP68 series filters. Other analog filtering schemes could be used, e.g., with continuous-time active filters such as might be implemented using the MAX 274 $8^{th}$-order filter by Maxim Integrated, Inc. of Milpitas, Calif., USA, or a switched-capacitor system such as the MAX26X series also by Maxim Integrated, Inc. The filters 306, 308 could also be implemented by digital signal processing systems in a number of configurations that could also be used to detect a range of non-respiratory movement that could be used for separate digital indications of non-respiratory movement of the subject and another entity such as a caretaker.

The power calculating and smoothing module 154 is implemented in this example by active rectifiers 310, 312, and a multi-stage log/log operational amplifier 314. The filtered signals from the filters 306, 308 are actively rectified by the rectifiers 310, 312, respectively, and passed to the multi-stage log/log amplifier 314. Each of the rectifiers 310, 312 may be implemented by a model MC3403 or TLE 208X series operational amplifier made by Texas Instruments. The multi-stage log/log amplifier 314 determines the log of the rectified output of the BPF 306 and the log of the rectified output of the LPF 308 and provides the result of each of these logarithms, which is the log of the power in each of the respective signals, to a difference amplifier 316. The multi-stage log/log amplifier 314 may be implemented by the dual logarithmic amplifier TL441ICN made by Texas Instruments. This integrated circuit has excellent linearity over a range of 30 dB which is sufficient to separate the two types of motion.

The comparison module 156 is implemented by the difference amplifier 316. The difference amplifier 316 is configured to determine a difference between the logarithm of the rectified output of the BPF 306 and the logarithm of the rectified output of the LPF 308. The difference between the logarithm of the rectified output of the BPF 306 and the logarithm of the rectified output of the LPF 308 is equivalent to the logarithm of the ratio of the power in these signals (i.e., the ratio of the power in the corresponding frequency ranges). This logarithmic difference is similar to the logarithm of the dimensionless number discussed above with respect to FIG. 7. The difference amplifier 316 may be implemented by a model MC3403 or TLE 208X series operational amplifier made by Texas Instruments.

The motion type module 158 is implemented in this example by comparators 318, 320. The comparators 318, 320 are connected to receive the output of the difference amplifier 316 and to determine motion of an entity other than the patient 22 (FIG. 1) and non-respiratory motion of the patient 22, respectively. The comparator 320 is configured to compare the output of the difference amplifier 316 to one or more appropriate thresholds for non-respiratory motion of the patient 22 and the comparator 318 is configured to compare the output of the difference amplifier 316 to an appropriate threshold, e.g., the upper threshold used by the comparator 320, to indicate whether motion of another entity is present. The thresholds used for the comparisons, and thus the separate indications of non-respiratory movement of the subject and of motion of another entity can be determined by scaling the outputs to the software-derived outputs, discussed with respect to FIG. 7, for equivalency. The output of each of the comparators 318, 320 is a digital indication of whether the respective type of movement is present. Either of the outputs of the comparators 318, 320 could be amplified and used to drive an LED indicator or other type of display or alarm. The output of the comparator 320 could be used to gate the respiratory output as an error condition, that is, respiratory motion may be ignored during periods of detected non-respiratory motion. The comparators 318, 320 may be implemented by the dual differential comparator model LM393 made by Texas Instruments.

The respiratory module 140 is implemented by the components shown in the section 330. The Phase A (PA) signal 92 (FIG. 2) is provided to comparators 332, 334 that are configured to detect if the Phase A signal is within the usable range of 0.5 to 4.5V of the comparators 54, 56 (FIG. 2). Voltages for comparison may be generated by a resistive network (not shown) connected between a positive digital power supply and ground. Both of the comparators 332, 334 are configured with hysteresis (e.g., a Schmitt trigger configuration) of approximately 0.05V, to reduce noise. The comparator 332 is configured to provide a high logic level output if the Phase A signal exceeds 4.5V, and the comparator 334 is configured to provide a high logic level output if the Phase A signal exceeds 0.5V. Thus, when the Phase A signal is in the usable range of 0.5 to 4.5V, the comparator 332 is at low logic level and the comparator 334 is at high logic level. The outputs of the comparators 332, 334 are connected to respective inputs of an exclusive-OR (XOR) gate 336. The XOR gate 336 is configured such that the output of the XOR gate 336 will be a high logic level if the output of the comparator 332 is at a low logic level and the output of the comparator 334 is at a high logic level, indicating that the Phase A signal is to be used for indicating/determining respiratory motion of the subject 22. If the Phase A signal is out of range, then the output of the XOR gate 336 is at a low logic level, indicating that the Phase B signal is to be used for indicating/determining respiratory motion of the subject 22. The output of the XOR gate 336 output is connected to a single-pole, double-throw (SPDT) analog switch 342 that is configured to select either a differentiated Phase A signal, when the output of the XOR gate 336 is at a high logic level, or a differentiated Phase B signal, when the output of the XOR gate 336 is at a low logic level. The output of the XOR gate 336 is also connected to an SPDT analog switch 344 that is configured to select either the polarity bit A (PbA) signal, when the output of the XOR gate 336 is at a high logic level, or the polarity bit B (PbB) signal, when the output of the XOR gate 336 is at a low logic level.

The PA and PB signals are conditioned by differentiator circuits 338, 340 that are configured to produce derivatives of the PA and PB signals, i.e., a differentiated PA signal (dPA) and a differentiated PB signal (dPB), respectively. The circuits 338, 340 are implemented by RC circuits and operational amplifiers each of whose gains are controlled by an input capacitor and combined input and feedback resistances, and have capacitive high-frequency blocking in a feedback loop. The gain and feedback values of each circuit are preferably trimmed so that the derivatives of the PA and PB signals are equal, as well as an input offset null so that when the derivatives of the PA and PB signals are zero, then the output of each of the differentiators 348, 350 is zero. The output of the switch 344, either PbA or the PbB, is connected to an input of a single-pole, double-throw switch 346, whose outputs are connected to inputs of an amplifier 348. The outputs of the switch 346 are connected to and control the amplifier 348 to either follow or invert an input of the amplifier 348, from the switch 342, according to the corresponding PbA or PbB. That is, the switch 346 is configured to output a "follow" signal if the polarity bit received from the switch 344 is a high logic level and to output an "invert" signal if the polarity bit received from the switch 344 is a low logic level. The amplifier 348, which may be implemented by a single operational amplifier, is configured to pass the differentiated signal received from the switch 342 while the amplifier 348 receives the "follow" signal from the switch 346 and to invert the differentiated signal from the switch 342 while the amplifier 348 receives the "invert" signal from the switch 346. Thus, an output 350 of the amplifier 348 is the differentiated Phase A signal (dPA) or the differentiated Phase B signal (dPB) corrected for sign by the PbA signal or the PbB signal. That is, the output 350 is the dPA signal while the PA signal is in the range of 0.5 to 4.5V and the PbA is a high logic level, is the dPA signal inverted while the PA signal is in the range of 0.5 to 4.5V and the PbA is a low logic level, is the differentiated Phase B signal (dPB) while the PA signal is outside the range of 0.5 to 4.5V and the PbB is a high logic level, and is the dPB signal inverted while the PA signal is outside the range of 0.5 to 4.5V and the PbB is a low logic level. The output 350 is connected to a clipping amplifier 352 that is configured to reduce high-frequency noise due to switching or non-respiratory movement. An output of the clipping amplifier 352 is connected to an integrator 354 that is configured to integrate the output of the clipping amplifier 352 to produce the respiratory output. The integrator 354 is configured to use a resistive element to return the integrated signal to baseline if there is a large output swing with non-respiratory movement.

Components of the section 330 may be implemented by the following example components. The comparators 332, 334 may be implemented by the comparator model LM393 noted above. An example of the XOR gate 336 is the XOR gate model SN74LVC1G286DBVR made by Texas Instruments. Each of the differentiator circuits 338, 340 may be implemented by a TLE 2081 operational amplifier made by Texas Instruments. An example of each of the switches 342, 344 is a single unit of the quad SPDT analog switch model DG333 made by Vishay® Intertechnology, Inc. of Malvern, Pa., USA. The switch 346 may be implemented with another unit of the quad DG333 integrated circuit. The operational amplifier 348 in this implementation has the properties of the TLE2082 integrated circuit made by Texas Instruments. The clipping amplifier 352 and the integrator 354 may each have the properties of the TLE2081 integrated circuit made by Texas Instruments.

Experimental Results

Figure 10:
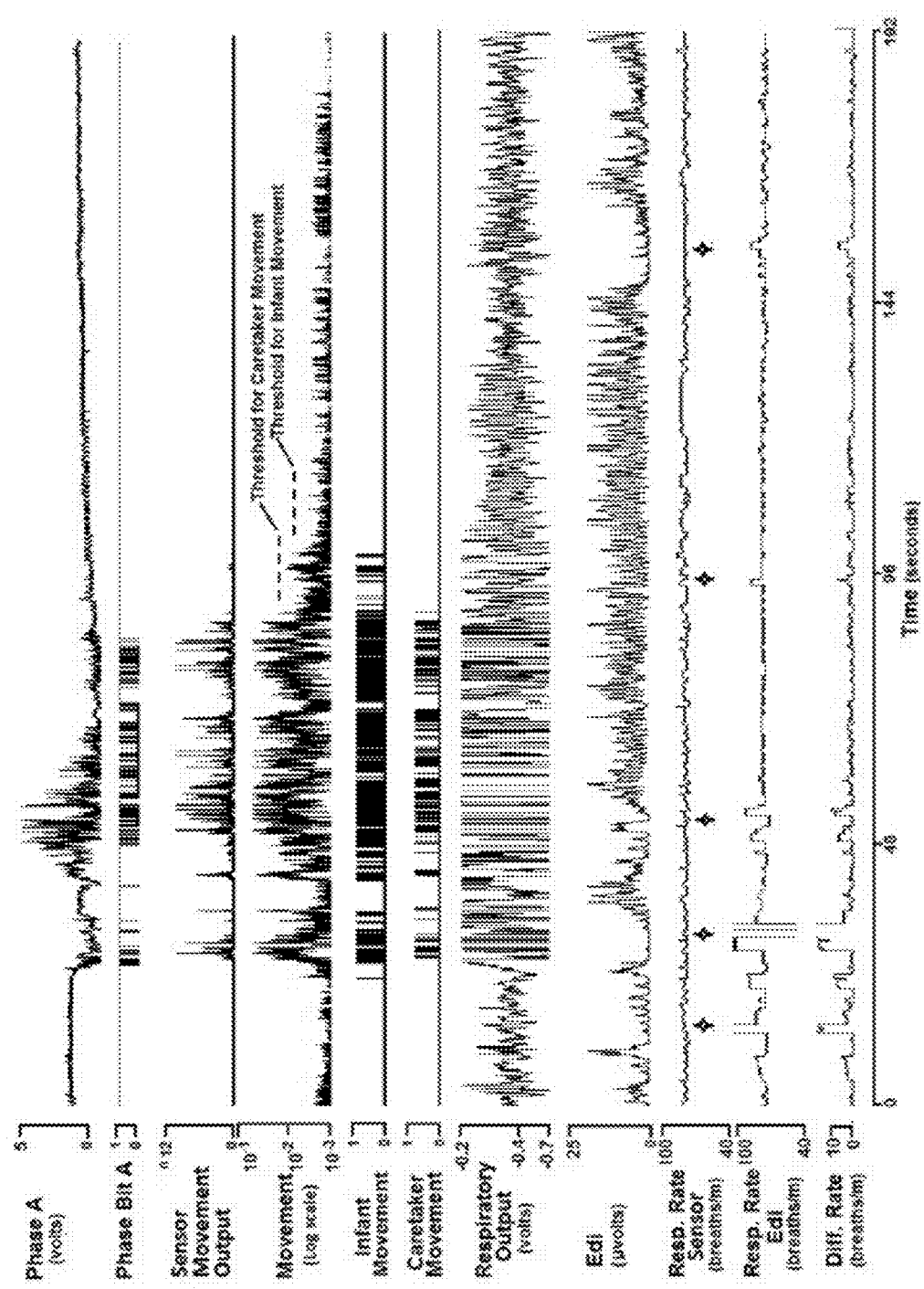
FIG. 10 is a composite diagram of experimental data derived from use of an example implementation of the system shown in FIG. 1.

Referring to FIG. 10, with further reference to FIG. 1, experimental results of an example implementation of the system 10 are shown. The subject 22 in this example was an infant weighing approximately two pounds. The signal analyzer 20 was implemented with the algorithm shown in FIG. 7. For simplicity and clarity, the Phase B signal and the Polarity bit B signal are not shown in FIG. 10. The plots in FIG. 10 show that the system 10 was able to provide indications of respiratory movement of the subject 22 (Respiratory Output), non-respiratory movement of the subject 22 (Infant Movement), and movement of an entity other than the subject 22 (Caretaker Movement). Further, a respiration rate was able to be determined (Resp. Rate Sensor (breaths/m).

Other Considerations

Other examples and implementations are within the scope and spirit of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations. Also, "motion" and "movement" are used herein interchangeably. Also, as used herein, "or" as used in a list of items prefaced by "at least one of" indicates a disjunctive list such that, for example, a list of "at least one of A, B, or C" means A or B or C or AB or AC or BC or ABC (i.e., A and B and C), or combinations with more than one feature (e.g., AA, AAB, ABBC, etc.).

While the discussion above described determining non-respiratory motion by comparing power in a non-respiratory motion frequency band with power in a respiratory motion frequency band, other techniques may be used to determine non-respiratory motion. For example, non-respiratory motion could be determined by analyzing power in the non-respiratory frequency band alone. For example, the amplitude of a band-pass-filtered signal for the non-respiratory frequency band could be compared against a threshold power value, with power values in the filtered signal being above the threshold indicating that non-respiratory motion is present. Thus, for example, stages 162, 164, 166, 176, 182 of FIG. 7 may be eliminated, and stage 184 modified to be a comparison of the power calculation of stage 174 against the threshold.

A statement that a value exceeds (or is more than or above) a first threshold value is equivalent to a statement that the value meets or exceeds a second threshold value that is slightly greater than the first threshold value, e.g., the second threshold value being one value higher than the first threshold value in the resolution of a computing system or the capability of analog comparators. A statement that a value is less than (or is within or below) a first threshold value is equivalent to a statement that the value is less than or equal to a second threshold value that is slightly lower than the first threshold value, e.g., the second threshold value being one value lower than the first threshold value in the resolution of a computing system.

As used herein, unless otherwise stated, a statement that a function or operation is "based on" an item or condition means that the function or operation is based on the stated item or condition and may be based on one or more items and/or conditions in addition to the stated item or condition.

Further, an indication that information is sent or transmitted, or a statement of sending or transmitting information, "to" an entity does not require completion of the communication. Such indications or statements include that the information is conveyed from a sending entity but does not reach an intended recipient of the information. The intended recipient, even though not actually receiving the information, may still be referred to as a receiving entity, e.g., a receiving execution environment.

Substantial variations may be made in accordance with specific requirements. For example, customized hardware might also be used, and/or particular elements might be implemented in hardware, software (including portable software, such as applets, etc.), or both. Further, connection to other computing devices such as network input/output devices may be employed.

The terms "machine-readable medium" and "computer-readable medium," as used herein, refer to any medium that participates in providing data that causes a machine to operate in a specific fashion. Using a computer system, various computer-readable media might be involved in providing instructions/code to processor(s) for execution and/or might be used to store and/or carry such instructions/code (e.g., as signals). In many implementations, a computer-readable medium is a physical and/or tangible storage medium. Such a medium may take many forms, including but not limited to, non-volatile media and volatile media. Non-volatile media include, for example, optical and/or magnetic disks. Volatile media include, without limitation, dynamic memory.

Common forms of physical and/or tangible computer-readable media include, for example, a floppy disk, a flexible disk, hard disk, magnetic tape, or any other magnetic medium, a CD-ROM, any other optical medium, punchcards, papertape, any other physical medium with patterns of holes, a RAM, a PROM, EPROM, a FLASH-EPROM, any other memory chip or cartridge, a carrier wave as described hereinafter, or any other medium from which a computer can read instructions and/or code.

Various forms of computer-readable media may be involved in carrying one or more sequences of one or more instructions to one or more processors for execution. Merely by way of example, the instructions may initially be carried on a magnetic disk and/or optical disc of a remote computer. A remote computer might load the instructions into its dynamic memory and send the instructions as signals over a transmission medium to be received and/or executed by a computer system.

The methods, systems, and devices discussed above are examples. Various configurations may omit, substitute, or add various procedures or components as appropriate. For instance, in alternative configurations, the methods may be performed in an order different from that described, and that various steps may be added, omitted, or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Specific details are given in the description to provide a thorough understanding of example configurations (including implementations). However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations provides a description for implementing described techniques. Various changes may be made in the function and arrangement of elements without departing from the spirit or scope of the disclosure.

Also, configurations may be described as a process which is depicted as a flow diagram or block diagram. Although each may describe the operations as a sequential process, many of the operations can be performed in parallel or concurrently. In addition, the order of the operations may be rearranged. A process may have additional stages or functions not included in the figure. Furthermore, examples of the methods may be implemented by hardware, software, firmware, middleware, microcode, hardware description languages, or any combination thereof. When implemented in software, firmware, middleware, or microcode, the program code or code segments to perform the tasks may be stored in a non-transitory computer-readable medium such as a storage medium. Processors may perform the described tasks.

Components, functional or otherwise, shown in the figures and/or discussed herein as being connected or coupled or communicatively coupled or as communicating with each other are communicatively coupled. That is, they may be directly or indirectly connected to enable communication between them.

Having described several example configurations, various modifications, alternative constructions, and equivalents may be used without departing from the spirit of the disclosure. For example, the above elements may be components of a larger system, wherein other rules may take precedence over or otherwise modify the application of the invention. Also, a number of operations may be undertaken before, during, or after the above elements are considered. Accordingly, the above description does not bound the scope of the claims.

Further, more than one invention may be disclosed.

The invention claimed is:

1. A method of detecting motion, the method comprising:
    transmitting a transmitted signal toward a subject, the transmitted signal being an ultrasound wave, the transmitted signal reflecting off the subject to produce a reflected signal;
    receiving the reflected signal and converting a form of the reflected signal from ultrasound wave to electrical;
    comparing, by a first phase comparator, the reflected signal to a first reference signal to determine a first reference phase signal indicative of a first phase difference between the first reference signal and the reflected signal, the first reference signal being associated with the transmitted signal;
    comparing, by a second phase comparator, the reflected signal to a second reference signal to determine a second reference phase signal indicative of a second phase difference between the second reference signal and the reflected signal, the second reference signal being out of phase with respect to the first reference signal;
    using the first reference phase signal only, from among the first reference phase signal and the second reference phase signal, when the second reference phase signal is in an out-of-specification zone of the second phase comparator, to determine respiratory motion of the subject; and
    using the second reference phase signal only, from among the first reference phase signal and the second reference phase signal, when the first reference phase signal is in an out-of-specification zone of the first phase comparator, to determine the respiratory motion of the subject.

2. The method of claim 1, further comprising using the first reference phase signal to determine non-respiratory motion by:
    filtering the first reference phase signal into a first portion within a first frequency range and a second portion within a second frequency range, the second frequency range being separate from the first frequency range; and
    analyzing a combination of the first portion of the first reference phase signal and the second portion of the first reference phase signal for the non-respiratory motion;
    wherein the non-respiratory motion includes at least one of non-respiratory motion of the subject or motion of an entity other than the subject.

3. The method of claim 2, wherein the analyzing the combination comprises determining a dimensionless magnitude associated with the combination.

4. The method of claim 3, further comprising:
    determining that the non-respiratory motion of the subject is occurring in response to the dimensionless magnitude being above a first threshold and below a second threshold; and
    determining that the motion of the entity is occurring in response to the dimensionless magnitude being above the second threshold.

5. The method of claim 3, wherein the determining the dimensionless magnitude comprises dividing a power value of the second portion of the first reference phase signal by a power value of the first portion of the first reference phase signal.

6. The method of claim 5, wherein the first portion of the first reference phase signal is within a frequency range between 0 Hz and 5 Hz, and the second portion of the first reference phase signal is within a frequency range between 22 Hz and 50 Hz.

7. The method of claim 2, wherein the first frequency range is associated with the respiratory motion of the subject and the second frequency range is associated with the non-respiratory motion.

8. The method of claim 1, wherein:
    the first reference signal and the transmitted signal are both derived from a common electrical drive signal;
    the using the first reference phase signal to determine the respiratory motion of the subject yields first indicia of the respiratory motion of the subject;
    the using the second reference phase signal to determine the respiratory motion of the subject yields second indicia of the respiratory motion of the subject; and
    the method further comprises:
        forming composite indicia of the respiratory motion of the subject comprising the second indicia of the respiratory motion of the subject corresponding to when the first reference phase signal is in the out-of-specification zone of the first phase comparator, and comprising the first indicia of the respiratory motion of the subject otherwise.

9. The method of claim 1, wherein the transmitting comprises transmitting a continuous wave ultrasound signal, having a fixed frequency between 30 KHz and 100 KHz, as the transmitted signal.

10. The method of claim 1, further comprising analyzing the first reference phase signal for non-respiratory motion by comparing a power level in a non-respiratory frequency range portion of the first reference phase signal with a threshold power level.

11. The method of claim 1, wherein the transmitted signal is of a transmit frequency, wherein the first reference signal is of the transmit frequency, and wherein the second reference signal is of the transmit frequency and is 90° out of phase with respect to the first reference signal.

12. A motion-detection system comprising: a driver configured to produce a drive signal and to produce, from the drive signal, a transmitter signal, a first reference signal, and a second reference signal:
  an ultrasound transmitter communicatively coupled to the driver and configured to transmit a transmitted signal toward a subject in response to the transmitter signal, the transmitted signal being an ultrasound wave;
  a receiver configured to receive a reflected signal and convert a form of the reflected signal from ultrasound wave to electrical;
  a phase difference device, including a first phase comparator and a second phase comparator, communicatively coupled to the driver and the receiver, configured to:
    compare the reflected signal to the first reference signal to determine a first reference phase signal indicative of a first phase difference between the first reference signal and the reflected signal, the first reference signal being associated with the drive signal; and
    compare the reflected signal to the second reference signal to determine a second reference phase signal indicative of a second phase difference between the second reference signal and the reflected signal, the second reference signal being out of phase with respect to the first reference signal; and
  a signal analyzer communicatively coupled to the phase difference device and configured to:
    use the first reference phase signal only, from among the first reference phase signal and the second reference phase signal, when the second reference phase signal is in an out-of-specification zone of the second phase comparator, to determine respiratory motion of the subject; and
    use the second reference phase signal only, from among the first reference phase signal and the second reference phase signal, when the first reference phase signal is in an out-of-specification zone of the first phase comparator, to determine the respiratory motion of the subject.

13. The system of claim 12, wherein the signal analyzer is further configured to:
  filter the first reference phase signal into a first frequency portion within a first frequency range and a second frequency portion within a second frequency range, the second frequency range being separate from the first frequency range; and
  analyze a combination of the first frequency portion of the first reference phase signal and the second frequency portion of the first reference phase signal to determine non-respiratory motion, the non-respiratory motion including at least one of non-respiratory motion of the subject or motion of an entity other than the subject.

14. The system of claim 13, wherein to determine the non-respiratory motion the signal analyzer is configured to:
  determine a dimensionless magnitude associated with the combination of the first frequency portion of the first reference signal and the second frequency portion of the first reference phase signal;
  provide an indication that the non-respiratory motion of the subject is occurring if the dimensionless magnitude is above a first threshold and below a second threshold; and
  provide an indication that the motion of the entity is occurring if the dimensionless magnitude is above the second threshold.

15. The system of claim 14, wherein the signal analyzer is configured to determine the dimensionless magnitude by dividing a power value of the second frequency portion of the first reference phase signal by a power value of the first frequency portion of the first reference phase signal.

16. The system of claim 15, wherein the first frequency portion of the first reference phase signal is within a frequency range between 0 Hz and 5 Hz, and the second frequency portion of the first reference phase signal is within a frequency range between 22 Hz and 50 Hz.

17. The system of claim 13, wherein the first frequency range is associated with the respiratory motion of the subject and the second frequency range is associated with the non-respiratory motion.

18. The system of claim 12, wherein:
  the second reference signal is a phase-shifted version of the first reference signal; and
  the signal analyzer is configured to form a composite subject respiratory signal by combining a first phase-differential portion of the first reference phase signal with a second phase-differential portion of the second reference phase signal, the first phase-differential portion of the first reference phase signal in the composite subject respiratory signal corresponding to a first linear range of the first phase comparator and the second phase-differential portion of the second reference phase signal in the composite subject respiratory signal corresponding to a second linear range of the second phase comparator, the signal analyzer being to form the composite subject respiratory signal with the second phase-differential portion and without the first phase-differential portion corresponding to when the first phase-differential portion of the first reference phase signal is outside the first linear range.

19. The system of claim 12, wherein the driver is configured to produce the transmitter signal with a frequency between 35 KHz and 45 KHz.

20. The system of claim 12, wherein the signal analyzer is configured to compare a power level in a non-respiratory frequency range portion of the first reference phase signal with a threshold power level.

* * * * *